United States Patent [19]
Kriesel et al.

[11] Patent Number: 5,385,546
[45] Date of Patent: Jan. 31, 1995

[54] MIXING AND DELIVERING SYSTEM

[75] Inventors: Marshall S. Kriesel, Saint Paul; Thomas N. Thompson, Richfield, both of Minn.

[73] Assignee: Science Incorporated, Bloomington, Minn.

[21] Appl. No.: 989,097

[22] Filed: Feb. 1, 1993

Related U.S. Application Data

[63] Continuation-in-part of Ser. No. 903,651, Jun. 24, 1992.

[51] Int. Cl.⁶ ............................................. A61M 37/00
[52] U.S. Cl. ................................... 604/85; 604/411; 604/412; 604/414; 604/416; 604/82; 604/83; 604/89; 604/90; 604/91
[58] Field of Search ......................... 604/56, 82–92, 604/406–407, 411–414, 416

[56] References Cited

U.S. PATENT DOCUMENTS

| | | |
|---|---|---|
| 3,488,327 | 1/1970 | Kollinsky et al. . |
| 3,583,950 | 6/1971 | Kollinsky et al. . |
| 4,072,566 | 2/1978 | Lynn . |
| 4,304,705 | 12/1981 | Heilmann et al. . |
| 4,392,851 | 7/1983 | Elias ................................ 604/88 |
| 4,451,619 | 5/1984 | Heilmann et al. . |
| 4,479,793 | 10/1984 | Urquhart et al. ............. 604/85 |
| 4,485,236 | 11/1984 | Rasmussen et al. . |
| 4,493,348 | 1/1985 | Lemmons ..................... 604/91 |
| 4,511,353 | 4/1985 | Theeuwes . |
| 4,539,294 | 9/1985 | Metcalfe et al. . |
| 4,639,286 | 1/1987 | Rasmussen et al. . |
| 4,737,560 | 4/1988 | Heilmann et al. . |
| 4,740,103 | 4/1988 | Theeuwes . |
| 4,740,197 | 4/1988 | Theeuwes . |
| 4,790,820 | 12/1988 | Theeuwes . |
| 4,871,824 | 10/1989 | Heilmann et al. . |
| 4,963,367 | 10/1990 | Ecanow . |
| 4,981,933 | 1/1990 | Fazio et al. . |
| 5,013,795 | 5/1991 | Coleman et al. . |
| 5,015,373 | 5/1991 | Carr et al. . |
| 5,045,615 | 9/1991 | Heilmann et al. . |
| 5,069,671 | 12/1991 | Theeuwes . |
| 5,081,197 | 1/1992 | Heilmann et al. . |
| 5,147,957 | 9/1992 | Kumar . |
| 5,205,821 | 4/1993 | Kruger et al. ................. 604/91 |
| 5,250,028 | 10/1993 | Theeuwes ....................... 604/85 |

FOREIGN PATENT DOCUMENTS

| | | |
|---|---|---|
| 20257758 | 3/1988 | European Pat. Off. . |
| 20392735 | 10/1990 | European Pat. Off. . |
| 20392783 | 10/1990 | European Pat. Off. . |
| 20433034 | 12/1990 | European Pat. Off. . |
| 20413551 | 2/1991 | European Pat. Off. . |
| 20430517 | 6/1991 | European Pat. Off. . |
| WO8807062 | 9/1988 | WIPO . |
| WO9207879 | 5/1992 | WIPO . |

*Primary Examiner*—Randall L. Green
*Assistant Examiner*—P. Zuttarelli
*Attorney, Agent, or Firm*—J. E. Brutnon

[57] ABSTRACT

An apparatus for separately storing a first component, such as a drug and for mixing this first component with a second component, such as a sterilized diluent, to form a beneficial agent which can be delivered to a patient from the container containing the second component. The device includes novel means for interconnecting a container, such as a glass vial containing a first component, such as a drug, with a second container such as a flexible bag containing the second component such as a parenteral liquid, and then for mixing the components under sterile conditions.

30 Claims, 14 Drawing Sheets

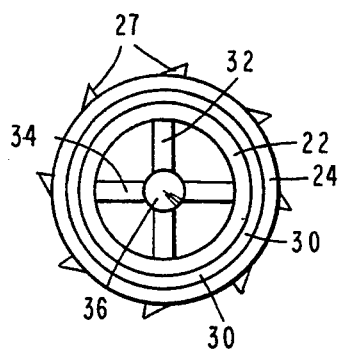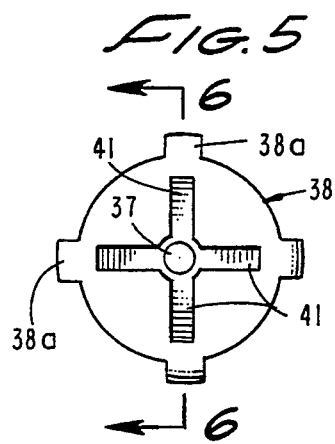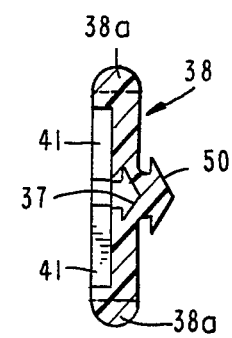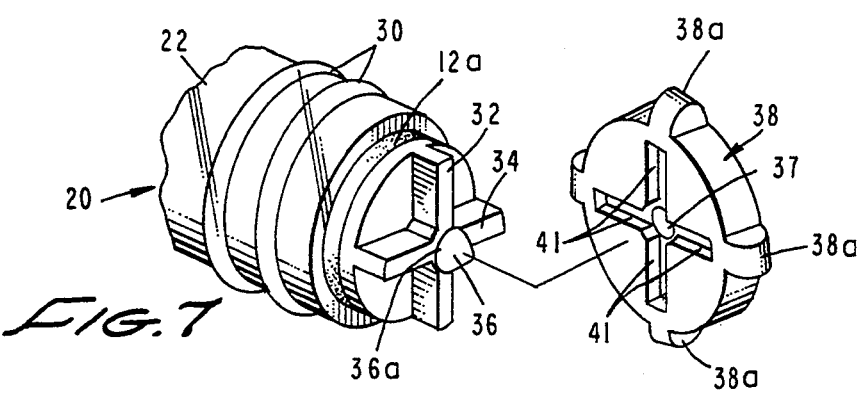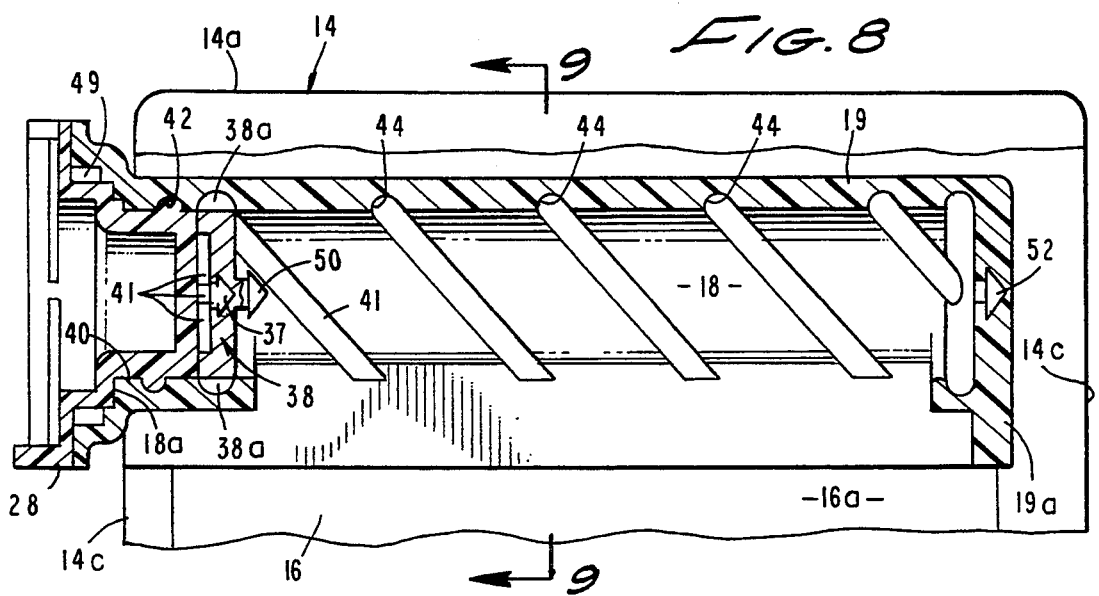

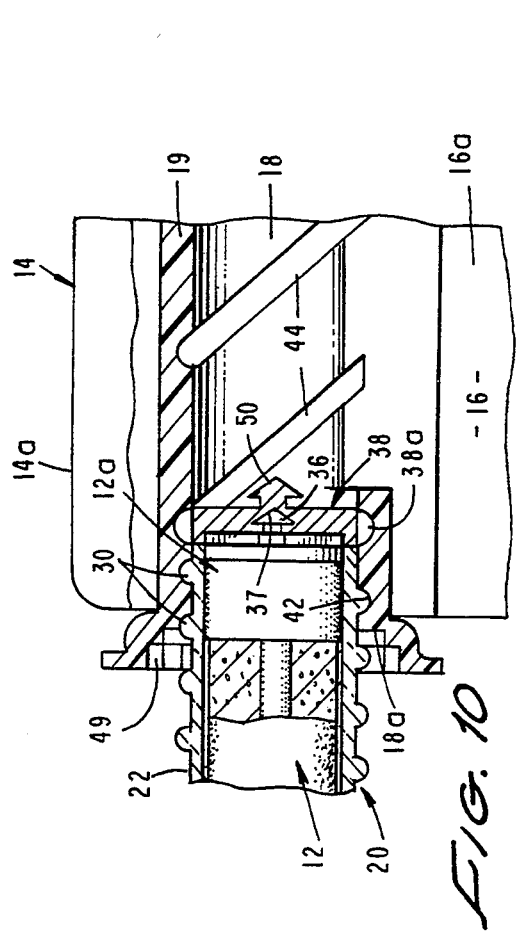
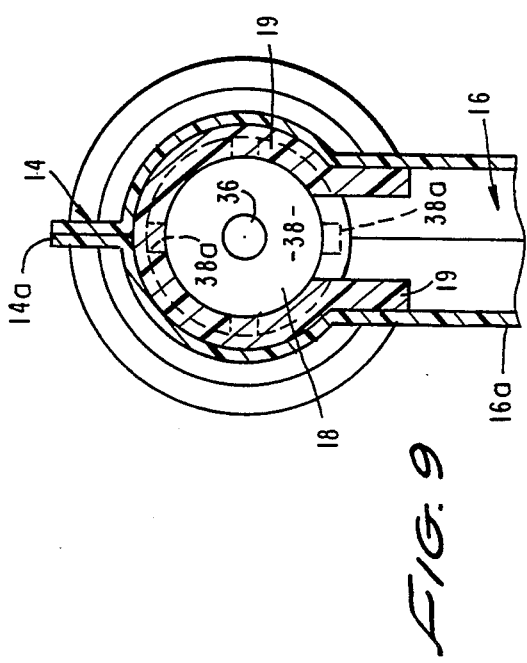
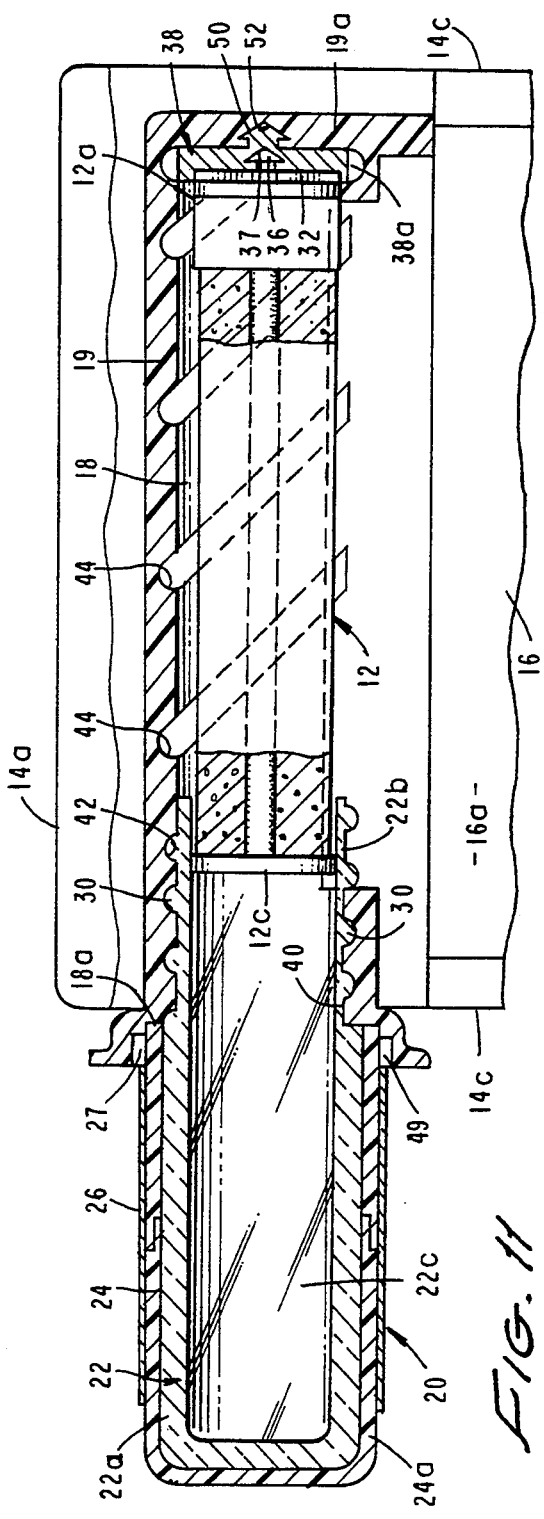

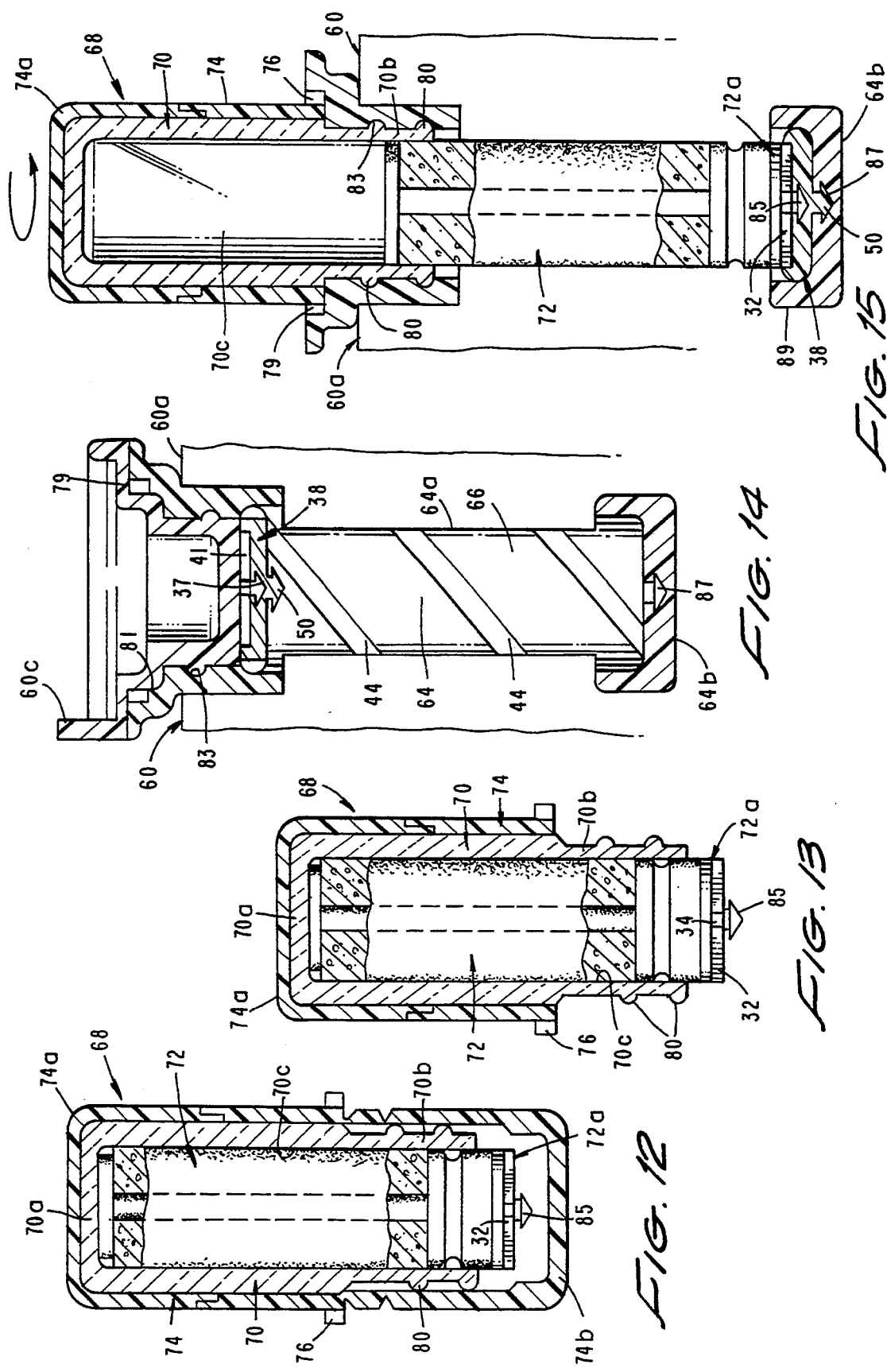

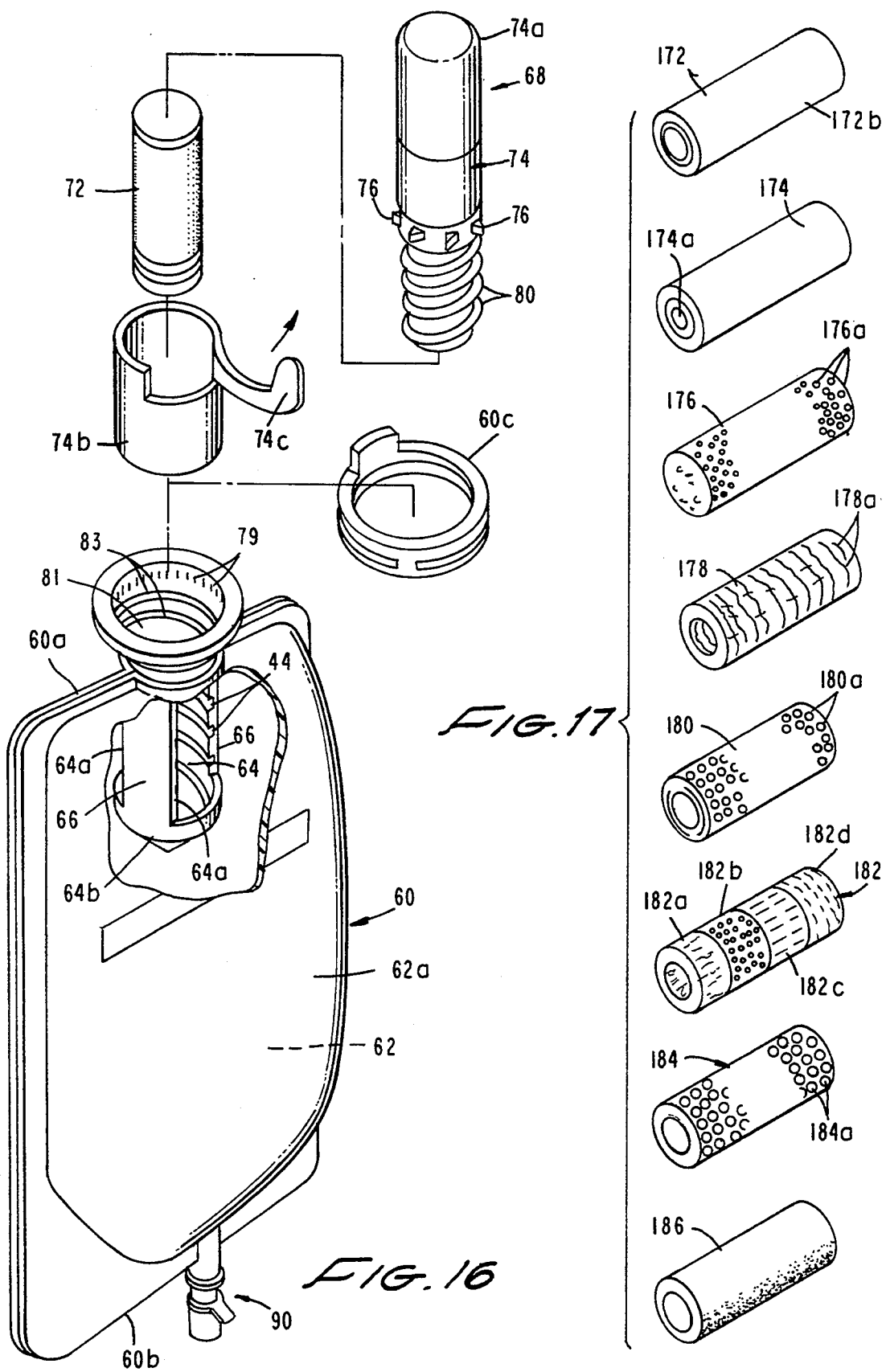

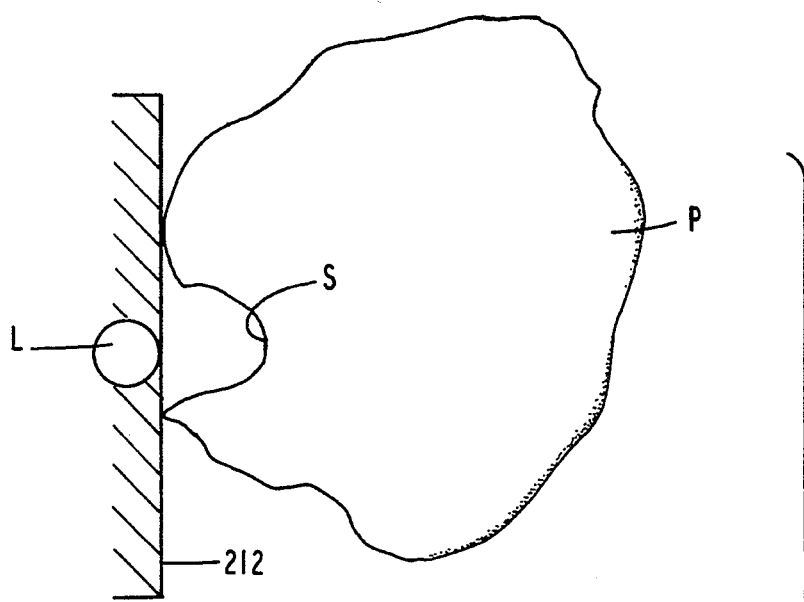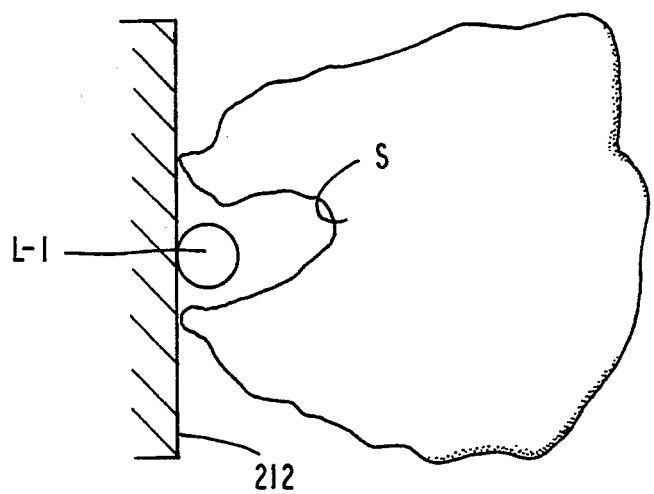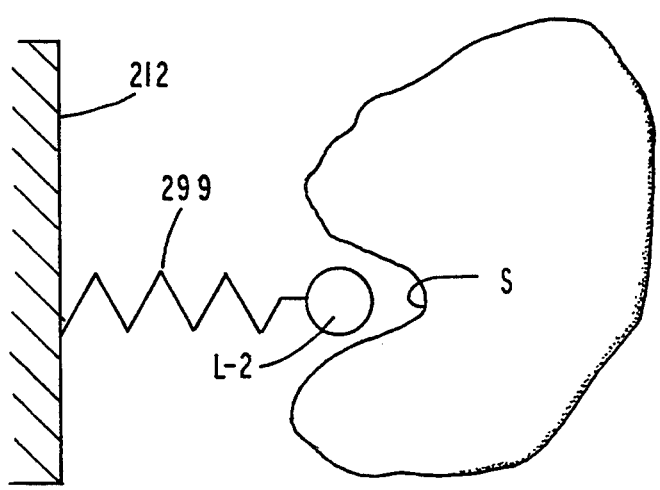
FIG. 33

MIXING AND DELIVERING SYSTEM

BACKGROUND OF THE INVENTION

This is a continuation in part application of co-pending application Ser. No. 07/903,651, filed Jun. 24, 1992.

FIELD OF THE INVENTION

The present invention relates generally to component mixing. More particularly, the invention concerns an apparatus for separately storing a first component, such as a drug and for mixing this first component with a second component, such as a sterilized diluent, to form a beneficial agent which can be delivered to a patient from the container containing the second component. The device includes novel means for interconnecting a container, such as a glass vial containing the first component, with a flexible bag containing the second component and then for mixing the components under sterile conditions.

DISCUSSION OF THE INVENTION

In the past, pharmaceuticals have been provided by drug manufacturers in sterilized vials, typically of glass construction. When the pharmaceuticals are in powder form, they are generally administered to the patient within a carrier liquid by standard intravenous procedures. Such carrier liquids include saline solution, dextrose solution and sterilized water.

Mixing of the powdered pharmaceuticals with the carrier liquid has been accomplished in several ways many of them being quite crude. For example, a common practice is to inject a quantity of the liquid carrier into the vial to dissolve the powdered component. Then using a cannula and syringe, the solution thus formed is injected into a larger container such as a flexbag containing the liquid carrier. This method is quite tedious and provides substantial opportunities for contamination and error.

In those instances where the pharmaceutical must be diluted before delivery to a patient, as is the case with powered pharmaceuticals, the pharmaceutical can also be injected directly into a container of diluent and the container then interconnected with a suitable administration set for intravenous delivery of the solution to a patient. As a general rule, the diluent is packaged in glass bottles, or flexible plastic containers such as those sold under the names MINI-BAG ™ and VIA-FLEX ® by Travenol Laboratories, Inc. of Deerfield, Ill. These containers are conveniently provided with administration ports for connection to the administration set which delivers the container contents from the container to the patient. The pharmaceutical is typically added to the container through some type of an inlet port or vial receptacle provided on the container.

Because infusion of medicaments is most often accomplished in a hospital environment, it is the nurse, doctor or medical technician who mixes the drug and diluent usually at one time shortly before administration of the drug to the patient. This mixing step can be time consuming and hazardous, as for example, when toxic drugs are involved. Further, since many of the prior art mixing devices are crude and imprecise, accurate, sterile and thorough mixing of the drug and the diluent is most difficult and time consuming. Accordingly, such devices are not well suited for use in the home environment.

Several types of closed drug delivery systems which are somewhat more sophisticated have recently been made available. These systems typically comprise a flexible container such as a plastic bag to which a glass drug vial can be easily coupled. The flexible container usually contains a liquid diluent and often includes a frangible member that allows fluid passage only when broken. As a general rule, when the drug vial is coupled with the flexible container, the stopper of the drug vial is pierced and the frangible member ruptured so as to allow sterile communication between the drug vial and the liquid diluent contents of the flexible container. Mixing of the drug with the diluent is accomplished by manipulation of the flexible container. Exemplary of prior art systems of this character are those disclosed in U.S. Pat. No. 4,583,971 issued to Bocquet, et al. and in U.S. Pat. No. 4,606,734 issued to Lyons. The Lyons apparatus includes a compressible chamber with a liquid component therein, the compressible chamber including gas trapping and reservoir compartments in open communication. The gas trapping compartment can be connected to a container such as a drug vial having a mixing component therein. After a pathway between the vial and the gas trapping compartment is opened, mixing is accomplished through manipulation of the compressible chamber.

Another very successful prior art, dual container system is described in U.S. Pat. Nos. 4,614,267 issued to Larkin and 4,614,515 issued to Tripp and Larkin. In this system, a flexible diluent container includes a tubular port which provides means for securing thereto a stoppered medicament vial as well as a stopper removal means. The stopper removal means includes an engagement element, or extractor, which is attached to a removable cover and seals the inner end of the port. In use, as the vial is advanced into the tubular port, the vial stopper moves into engagement with the extractor which grips the stopper enabling it to be pulled from the vial as the cover is pulled from the port. Once the stopper has been removed from the vial, the powered contents of the vial, such as a lyophilized drug, can be dumped into the diluent in the bag and mixed therewith through manipulation of the bag.

Still another type of component mixing device is disclosed in U.S. Pat. No. 4,467,588 issued to Carveth. The Carveth device includes two sealed chambers having a frangible sterilized connection therebetween. One chamber carries the liquid component and the other carries a sealed vial containing the second component. The frangible connection provides a sterile pathway for intermixing the components.

The apparatus of the present invention offers numerous advantages over the prior art devices by providing a closed system for separately storing and selectively intermixing a wide variety of different types of medicaments and other beneficial agents with a diluent or other parenteral fluid under completely sterile conditions. The beneficial agents, such as drugs and biologically active materials are typically immobilized on a suitable substrate which is preferably stored within a glass vial until shortly before the time that the beneficial agent is to be administered to the patient. The vial along with the substrate can be quickly and easily interconnected with a sterile chamber which is disposed in fluid communication with the diluent chamber of a flexible bag so that the substrate can be presented to the diluent in a manner to permit separation and release of the beneficial agent and its thorough mixing with the diluent.

SUMMARY OF THE INVENTION

The preferred form of the apparatus of the present invention for intermixing first and second components includes a flexible container having a fluid reservoir for containing a liquid component, such as a diluent. In fluid communication with the reservoir is a sterile mixing chamber into which the assembly containing the first component, such as a beneficial agent, can be introduced. The assembly carrying the beneficial agent includes a support structure to which the beneficial agent is removably affixed and a housing, such as a glass vial, which serves to contain the support structure within a sealed, sterile environment. Upon mating the assembly with the flexible container, the substrate carrying the beneficial agent is automatically moved into a position within the mixing chamber so that the substrate is directly exposed to the fluid reservoir that contains the diluent. Upon appropriate manipulation of the flexible container, the diluent will flow through and about the substrate in a manner such that the beneficial agent, removably carried thereby, is separated from the substrate and thoroughly intermixed with the diluent to form the solution to be delivered to the patient via an administration set that is connected to the flexible container.

It is an object of the present invention to provide an apparatus of the character described in the preceding paragraph which provides the opportunity to add to a diluent or other parenteral fluid contained within a flexible solution container (flexbag), selected elements, chemical compounds and biologically active materials, including drugs, medicaments, biological agents, and other therapeutic agents (additives). This addition is accomplished by removably affixing the selected additives to various forms of support structures which can be placed within a mixing chamber disposed proximate the liquid reservoir of the flexbag and in the path of the fluid forced from the fluid reservoir when the flexbag is manipulated. In this way, the diluent within the flexbag can expeditiously be rendered therapeutically active upon hydration of the additive carried by the substrate which is disposed within the mixing chamber.

Another object of the invention is to provide an apparatus of the character described in which the adding means, including the substrate which carries the first component, or additive, is maintained within a completely sterile environment, such as a sealed or stoppered glass vial, until immediately prior to the controlled mixing of the first and second components.

Another object of the invention is to provide an apparatus of the class described in which a wide variety of selected additives can be removably affixed to the substrate that is introduced into the mixing chamber of the flexbag assembly for controlled intermixing with the liquid contained within the fluid reservoir of the flexbag assembly.

Another object of the invention is to provide a device of the aforementioned type in which toxic or other hazardous compounds, including those with short therapeutic lives can be separately and safely stored until immediately prior to their use following being intermixed with the liquid compound contained with the separate flexible bag container.

Another object of the invention is to provide a device of the character described in the preceding paragraph in which toxic or other hazardous compounds which are to be intermixed with the liquid component can be separately and safely handled during the manufacture of the substrate portion of the device and in which the substrate carrying the hazardous materials can, following manufacture, be safely stored within a sealed glass vial until time of use.

Another object of the invention is to provide a device of the class described in which the additive or beneficial agent components, such as a drug, can be uniformly deposited or otherwise removably affixed to the additive support in a manner to maximize immediate and substantially complete separation of the additive and complete intermixing thereof with the liquid component.

Still another object of the invention is the provide a device of the character described in the preceding paragraphs which is easy to use, is highly reliable, and is inexpensive to produce in quantity so that the device can be disposed of after use.

BRIEF DESCRIPTION OF THE DRAWINGS

FIG. 4 is an end view of the container shown in FIG. 3.

FIG. 5 is an end view of the transport disc of the apparatus which is carried within the inlet of the container, such as a flexible bag, which contains the first component to be mixed.

FIG. 6 is a cross-section view taken along lines 6—6 of FIG. 5.

FIG. 7 is a fragmentary generally perspective view illustrating the manner in which the container containing the first component is interconnected with the transport disc of the second container.

FIG. 8 is a cross-sectional view of the upper mixing chamber of the container, such as a flexible bag, that contains the first component showing the transport disc in an initial position within the inlet of the mixing chamber.

FIG. 9 is a cross-section view taken along lines 9—9 of FIG. 8.

FIG. 10 is a cross-sectional view illustrating the initial mating of the container containing the first component with the transport disc of the container containing the second component.

FIG. 11 is a fragmentary view similar to FIG. 10 but illustrating the movement of the components of the container containing the first component as the container is mated with the container containing the second component.

FIG. 12 is a cross-sectional view of an alternate form of the container, such as a glass vial, which contains the first component to be mixed.

FIG. 13 is a cross-sectional view similar to FIG. 12 but showing the appearance of the container after the sealing cap has been removed.

FIG. 14 is a fragmentary, cross-sectional view of an alternate form of the second container of the apparatus, such as a flexible bag, illustrating the construction of the mixing chamber which, in this instance, is generally vertically oriented rather than horizontally oriented as was the case with the first embodiment of the invention.

FIG. 15 is a fragmentary cross-sectional view illustrating the mating of the container containing the first component with the container containing the second component.

FIG. 16 is an exploded generally perspective view of the alternate form of the container which contains the first component illustrating the manner in which the container containing the second component is interconnected.

FIG. 17 is a generally perspective view of various configurations of supports adapted to removably carry the first component.

FIGS. 33, 34, 35, and 36 are general diagrammatic views illustrating various means for affinity attachment of ligands, protein molecules and enzymes to the substrates.

DESCRIPTION OF THE INVENTION

Figure 1:
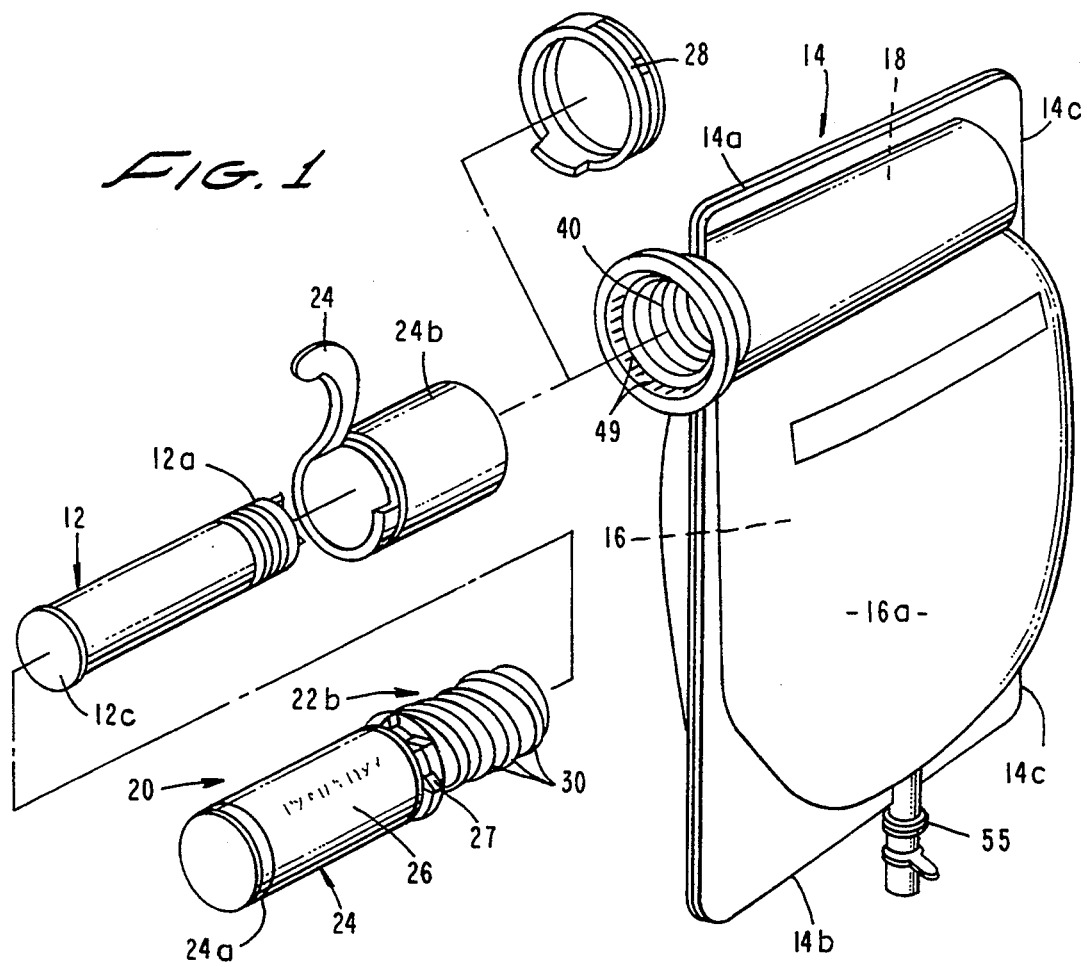
FIG. 1 is a generally perspective exploded view of one form of the mixing and delivery system of the present invention.

In the paragraphs which follow, wherein the apparatus of the invention will be discussed, the following terms will have the following meanings:

Element—any of the fundamental substances that consist of atoms of only one kind and that singly or in combination constitute all matter.

Additive—the element, compound, substance, agent, biologically active material, or other material which is to be added to the fluid contained in the reservoir of the device of the invention.

Parenteral Fluid—any solution which may be delivered to a patient other than by way of the intestines, including water, saline solutions, alkalizing solutions, dextrose solutions, acidifying solutions, electrolyte solutions, reagents, solvents and like aqueous solutions.

Beneficial Agents—any drug, medicament, pharmaceutical, medical polymer, enzyme, element, chemical compound or other material useful in the diagnosis, cure, mitigation, treatment or prevention of disease and for the maintenance of the good health of the patient.

Biologically Active Material—a substance which is biochemically, immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such biochemical compounds biologically functioning as antibodies, antigenic substances, enzymes, co-factors, inhibitors, lectins, hormones, hormone producing cells, receptors, coagulation factors, anti-fungal agents, growth enhancers, histones, peptides, vitamins, drug, cell surface markers and toxins, among others known to those skilled in the art. Of the group of biologically active materials described, proteins are of utmost current interest because of the large molecule genetically engineered biopharmaceuticals as those species to be immobilized on the additive carriers hereinafter to be described. A discussion of the use of biomosic polymers as carriers for biologically active materials is set forth in European Patent Application 0,430,517 A2.

Adding Means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a functional support, or carrier, an anchorage, a deposition site or element holder, with or without some type of intermediate matrix.

Additive Presentation Means—any means such as a functional support or substrate for presenting the additive to the fluid flowing through the device. The functional substrate can comprise a polymer, copolymer, and inter-polymer, a ceramic, a crystal sponge, a carbon based matrix, a celullosic, glass, plastic biomosaic polymers, azlactone-functional polymer beads, adduct beads, carboxylate-functional polymer beads, gums, gels, filaments and like carriers.

The adding means of the invention can take several different forms such as those illustrated in FIG. 17. However, in its preferred form, the adding means comprises a cylindrically shaped, microporous, polymeric functional support structure 12 (FIG. 2) to which various additives, including beneficial agents such as drugs, biologically active materials, and various chemical elements and compounds can be releasably connected. Structure 12 can include porous channels that extend completely through the substructure forming micropores on the surface of the polymers and throughout the substrate structure. These additives are carried by the structure in a manner such that, as the liquid contained within the second container, which may comprise a diluent, a reagent or other aqueous solvent, flows around, about and through the support assembly, in the manner presently to be described, the additives will be presented to the liquid, separated from the support assembly and efficiently added and intermixed with the liquid.

The additives themselves can also take various physical forms including liquid, solid, granular, powder, particle, microparticles, gel, wax hydrocolloid carriers, such a gum film, tablet, crystalline, emulsions, microcrystalline, microcapsules, microspherical, spray dried compounds and lypohilized compounds and saturants. The additives can be removably connected to, immobilized on, impregnated within or supported by support means in a number of ways. The additives can be chemically or mechanically attached, affixed, or bound directly or indirectly through cooperation with an intermediate matrix. They can be captured, affixed, linked, or cross-linked, anchored to the surfaces of the support, or surface active agent, or they can be absorbed, reaction catalyzed, electrostatically encapsulated, attached by chemical modification in to the carrier surface, polymerized on or through the carrier, localized, entrapped, deposited suspended or occluded within voids, cells, tubules and interstices formed in the support. One important method for removably affixing the additive to the functional support means includes treating the functional support means with a compound having reactive functional groups such as azlactone functional compounds with their high binding capacity. In certain applications, the biologically active material can be bound at the surfaces of biomosaic polymers in the manner described in EPO Patent No. 0 430 517 A2. Similarly, graft copolymers can be used in the manner described in U.S. Pat. No. 5,013,795 issued to Coleman, et al. In this way complexing agents, catalysts and biological materials such as enzymes or other proteins as well as biomacromolecules can be attached to the carrier.

Similarly, the additives can be immediately separated from the functional support and added to or intermixed with the liquid flowing through the device by one or more of various mechanisms, including chemical reaction, dissolution, debinding, delinking bioseparation, diffusion, washing, disintegration, erosion, disassociation, desorbsion, solubilization, leeching, enzymatic cleavage, biological reaction, osmosis, separated from ring opening materials and like separation means.

Figure 2:
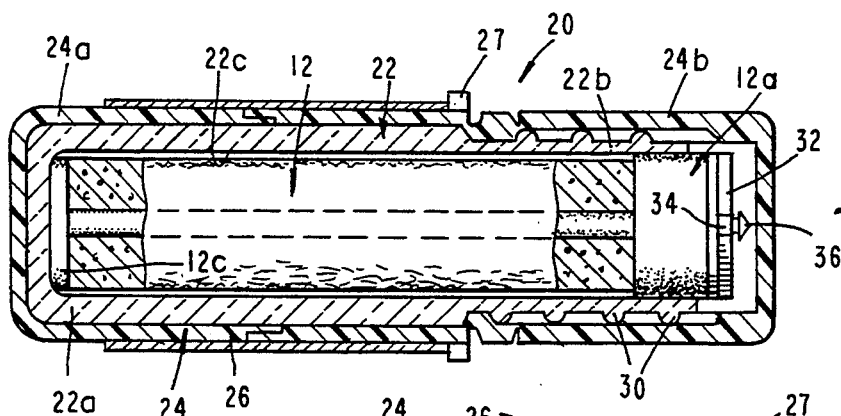
FIG. 2 is an enlarged cross-sectional view of the container such as a closed and stoppered glass vial which contains one of the components to be mixed.

Referring now to the drawings and particularly to FIGS. 1 and 2, one form of the apparatus of the invention for controllably intermixing the first component with the second liquid component comprises a container 14 having a fluid reservoir portion 16 for containing the second component and a mixing chamber 18 within which the first and second components can be intermixed. Reservoir portion 16 is formed by sealably interconnected flexible walls 16a and mixing chamber 18 is formed by rigid walls 19 (FIGS. 8 and 9). As best seen in FIG. 9, chamber 18 is in fluid communication with the upper end of reservoir portion 16. Container 14 further includes top, bottom and side edges 14a, 14b, and 14c with mixing chamber 18 being disposed proximate top edge 14a and extending generally parallel to top and bottom edges 14a and 14b.

The apparatus also comprises adding means, as earlier defined herein, for presenting the first component to the second component for intermixing the two components. In the embodiment of the invention shown in FIGS. 1 and 2, the adding means comprises the previously identified support 12 upon which the first component is removably affixed. The adding means also includes a container assembly 20 for containing support 12 and connector means for connecting the container assembly 20 to the mixing chamber so that support 12 can be exposed to fluid introduced into the mixing chamber upon manipulation of the flexible container 14. Container 14 is preferably constructed of flexible plastic sheets which are interconnected along their edges in a manner well known in the art to form the fluid reservoir. The mixing chamber preferably comprises a tubular shaped plastic structure which is sealably encapsulated within the container body in a manner well known to those skilled in the art.

As best seen in FIG. 2, container assembly 20 comprises a glass vial 22 which is surrounded by a protective covering 24, such as a thin plastic. Protective covering 24 is fabricated in two parts and includes a body portion 24a which encapsulates the non-threaded body portion 22a of the glass vial and a removable cover portion 24b which initially sealably encapsulates the threaded, open end 22b of the glass vial. Circumscribing cover 24 is a label 26. Provided on covering 24 intermediate its ends are a plurality of circumferentially spaced locking teeth 27, the purpose of which will presently be described.

As illustrated in FIG. 1, protective cover 24b comprises a tear-off type portion which can be removed from the glass vial assembly by pulling on a tear tab 24c. Similarly, the opening, or inlet port, of the mixing chamber portion of the flexible container 14 is initially sealed by a sterile tear-off cap 28. These types of tear off caps are of a character well known in the art.

Figure 3:
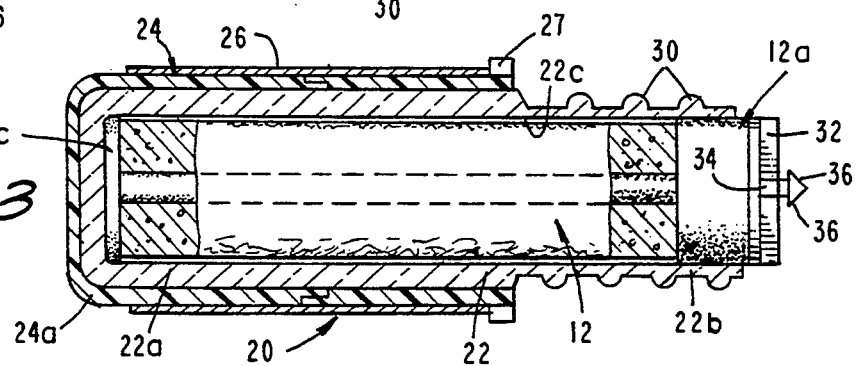
FIG. 3 is a cross-sectional view similar to FIG. 2, but showing the container containing the second component after the protective cover which seals the container has been removed.

Referring to FIGS. 3 and 4 it can be seen that after tear-off cover 24b is removed from the vial assembly, external threads 30, which are provided on glass vial 22, are exposed. Similarly, the forward most, or outboard extremity 12a of support assembly 12 is exposed. Turning to FIG. 7 it can be seen that outboard end 12a of support 12 is uniquely configured to include perpendicularly disposed, diametrically-extending ridges 32 and 34. Provided proximate the crossing point of ridges 32 and 34 is an umbrella-like locking protuberance 36 which is adapted to interlock within a cavity 37 provided in a transport disc 38. Transport disc 38 is initially positioned within the inlet port 40 of mixing chamber 18 and functions to seal the mixing chamber to atmosphere following removal of the tear cap 28 (see also FIG. 8). Disc 38 is also provided with a pair of perpendicularly extending grooves 41 which are adapted to closely receive ridges 32 and 34 when the support is connected to the disc.

Turning now particularly to FIG. 8, wall 19 of mixing chamber 8 is provided with two sets of internal threads identified by the numerals 42 and 44 respectively which are of substantially different pitch with threads 44 having a considerably greater pitch than threads 42. Threads 42 are adapted to mate with external threads 30 provided on vial 22 to enable interconnection of the container assembly 20 with the flexible bag 14. On the other hand, transport disc 38 is adapted to mate with coarse threads 44. For this purpose, circumferentially spaced rounded protuberances are provided on disc 38a (FIGS. 5 and 7), which protuberances are closely receivable within threads 44. In this regard it is to be noted that disc 38 is initially positioned within threads 44 at a location proximate the inlet port 40 of the mixing chamber. As previously mentioned, with this construction, the inlet port remains sealed to atmosphere when cover 28 is removed, thereby preventing the interior of chamber 18 from becoming contaminated prior to the container assembly being connected to the flex bag in a manner next to be described.

In using the apparatus of the present invention, tear cap 24b is first removed from the vial assembly 20 by griping tear strip 24c (FIG. 1) and pulling outwardly. With cap 24b removed, the container assembly has the appearance shown in FIG. 3. Next, the flex bag port cover or cap 28 is removed from the inlet port of the flexible bag assembly 14 so as to expose the mouth of the port in the manner illustrated in FIG. 1. As indicated in FIG. 9, disc 38, which is preferably assembled with the flex bag subassembly at the time of its manufacture, rests within the outboard end of threads 44 and functions to sealably close inlet port 40 to atmosphere. Transport disc 38 comprises a portion of the transport means of the present embodiment of the invention and, in a manner presently to be described, functions to advance support 12 inwardly of the mixing chamber upon rotation of vial 22 relative to the connector port or inlet port 40 of the flex bag 14.

Turning now to FIG. 10, mating of the container assembly 20 with the flex bag assembly 14 is accomplished by inserting the outboard, or threaded end of the glass vial 22 into port 40 in the manner shown in FIG. 10. Upon insertion of the container assembly 20 into the connector port, threads 30 will mate with threads 42 and simultaneously the forward end 12a of support 12 will move into engagement with transport disc 38. As the forward end 12a of the support 12 moves into mixing chamber 18, ridges 32 and 34 will be received within grooves 41 and protuberance 36, which is provided on the support 12, will be lockably received within aperture 37 provided on disc 38. Umbrella-shaped protuberance 36 will be securely interlocked within aperture 37 of disc 38, which aperture is configured in the manner best seen in FIG. 6 to lockably engage protuberance 36 so that the resiliently deformable flange portion 36a of the protuberance will prevent withdrawal of support 12 from the transport disc.

With the container assembly 20 in the position shown in FIG. 10, rotation of the assembly will cause the component parts of the assembly to move inwardly into the mixing chamber in the manner shown in FIG. 11. More particularly, threads 30 which are provided on the glass vial will advance within internal threads 42 provided proximate the inlet port or connector port of flex bag assembly 14. At the same time ridges 32 and 34, which have been received with channels 41 of the transport disc, will impart rotation to disc 38. Because threads 44 are much more coarse than threads 42, rotation of the container assembly 20 will cause disc 38 and support 12, which is interconnected therewith by protuberance 36, to advance rapidly within chamber 18 from the first position shown in FIG. 10 to the second position shown in FIG. 11. As support 12 advances, it will move telescopically outwardly of the internal chamber 22a of glass vial 22, with the resiliently deformable, piston-like end portion 12c sliding along the internal wall of chamber 22a. At the point at which support 12 reaches the second position shown in FIG. 11, locking protuberances 27 provided on container assembly 20 will interlock with grooves 49 provided within inlet port 40 (FIG. 1) thereby locking the container assembly to the flex bag.

It should be noted that transport disc 38 is also provided with an umbrella-like protuberance 50 which is lockably receivable within a corresponding configured aperture 52 provided in end wall 19a of mixing chamber 18. Once again, protuberance 50 and its receptacle or aperture 52 are so configured that upon movement from the first position shown in FIG. 10 to the second position shown in FIG. 11, support 12 will be securely locked in place within the mixing chamber in the manner best seen in FIG. 11. In this position the open end of vial 22 sealably engages an internal shoulder 18a provided on the mixing chamber.

With support 12 securely locked and fluid-tight sealed into position within mixing chamber 18, and with container assembly 20 lockably connected and fluid-tight sealed to inlet port 40 of the flex bag, manual manipulation of the flexible film portion of side walls 16a of the reservoir portion 16 of the flexible bag will cause the fluid within the reservoir, such as a diluent or other parenteral fluid, to flow into mixing chamber 18 and rapidly move around, about and through substrate 12 in a manner to expeditiously and completely remove the additive from the substrate and thoroughly intermix it with the liquid component.

After the first and second components have been substantially mixed and the combined solution thus formed has returned to reservoir 16, the solution can be withdrawn from the flex bag through an appropriate administration set (not shown) that has been interconnected with outlet port 55 (FIG. 1).

Referring now to FIGS. 12 through 16 and particularly to FIG. 16, another form of the apparatus of the invention for controllably intermixing the first component and the second liquid component is there shown. This embodiment is similar to the previously discussed embodiment and comprises a flexible container 60 having a fluid reservoir portion 62 with flexible side walls 62a for containing the second component. Container 60 also has a mixing chamber 64 formed by rigid walls 66. As before, chamber 64 is in fluid communication with reservoir portion 62 via open side portions 64a. In this later form of the invention, it is to be observed that the mixing chamber extends generally perpendicular to, rather than parallel with, top and bottom edges 60a and 60b. Save for this fact this second embodiment of the invention is of basically the same construction and operates in essentially the same way as the embodiment of the invention shown in FIGS. 1 through 12. Accordingly like numbers are used in FIGS. 12 through 16 to identify like components.

As best seen in FIG. 12, the container assembly 68 of this embodiment of the invention comprises a glass vial 70 which carries within its internal chamber a support 72. Vial 70 is surrounded by a plastic overcover sheath 74 which includes a body portion 74a which encapsulates the non-threaded body portion 70a of the glass vial and a portion 74b which sealably encapsulates the threaded, open end 70b of the glass vial. Circumscribing the intermediate portion of covering 74 is a collar having circumferentially spaced locking teeth 77 of the character previously described and as shown in FIG. 1 for locking the container assembly to the flexible bag. Overcover 74 is constructed in two mating parts which are appropriately bonded together.

Overcover 74b comprises a tear-off type cover end portion which, as before, can be removed from the glass vial assembly by pulling on a tear tab 74c (FIG. 16). Similarly, the opening, or inlet port, of the mixing chamber portion of the flexible container is initially sealed by a sterile tear-off cap 60c of the same type illustrated in FIG. 1 and of a character well known in the art.

Referring to FIG. 13 it can be seen that after tear-off cover portion 74b is removed from the vial assembly, external threads 80 which are provided on glass vial 70, are exposed. Similarly, the downwardly extending, or outboard extremity 72a of support 72 is exposed. The outboard end 72a of support 72 is configured in the same manner as end 12b of support 12 and interlocks within a cavity 37 provided in transport disc 38 which is carried within the inlet port of mixing chamber 64.

Mixing chamber 64 is also provided with two sets of internal threads which cooperate with threads 80 and with disc 38 in the same manner as previously described in connection with the earlier embodiment.

In using the apparatus of this second form of the intention, tear cap 74b is first removed from the vial assembly and the flex bag port cover or cap is removed from the inlet port 81 of the flexible bag assembly 68 so as to expose the vertically extending mouth of the port in the manner illustrated in FIG. 14. As indicated in FIG. 14, disc 38, rests within the outboard end of threads 44 and functions to sealably close inlet port 81 to atmosphere. As before, disc 38 functions to advance support 72 inwardly of the mixing chamber upon rotation of vial 70 relative to the connector port or inlet port 81 of the flex bag.

Turning to FIGS. 14 and 15, mating of the container assembly 68 with the flex bag assembly is accomplished as before by inserting the outboard, or threaded end of the glass vial 70 into port 81. Upon insertion of the container assembly into the connector port, threads 80 will mate with the first internal threads 83 and the forward end of support 72 will move into locking engagement with transport disc 38. As the forward end of the support moves into the mixing chamber, protuberance 85 which is provided on the support 72, will be lockably received within aperture 37 provided in disc 38. Rotation of the container assembly will cause the component parts of the assembly to move downwardly into the mixing chamber in the manner shown in FIG. 15. More particularly, threads 80 which are provided on the glass vial will advance within internal threads 83 provided proximate the inlet port or connector port of flex bag assembly. At the same time ridges 32 and 34, which have been received with channels 41 of the transport disc, will impart rotation to disc 38 with the resiliently deformable, piston-like end portion of the support sliding along the internal wall of chamber 22a. At the same time that support 12 reaches the second position shown in FIG. 11, locking protuberances 76 provided on container assembly 68 will interlock with grooves 79 provided within inlet port 81. Continued rotation of the container assembly 68 will cause disc 38 and support 72, which is interconnected therewith by protuberance 36 to advance rapidly within chamber 64 from a first position to a second position shown in FIG. 15. As support 72 advances into the mixing chamber, it will move telescopically outwardly of the internal chamber of the glass vial.

Once again, since transport disc 38 is provided with a generally umbrella-shaped protuberance 50 which is lockably receivable within an aperture 87 provided in end wall 64b of the mixing chamber, movement from the first starting position to the second position shown in FIG. 15, will result in support 72 being securely locked in place within the mixing chamber in the manner best seen in FIG. 15.

With support 72 securely locked into position within mixing chamber and with container assembly 68 lockably connected to inlet port 81 of the flex bag, manual manipulation of the side walls of the reservoir portion of the flexible bag will cause the fluid within the reservoir, such as a diluent or other parenteral fluid, to flow into mixing chamber 64 and rapidly move around, about and through support 72 in a manner to expeditiously release and substantially remove the additive from the support and thoroughly intermix it with the liquid.

After the first and second components have been mixed and the solution thus formed has returned to reservoir 62, the solution can be withdrawn from the flex bag through an appropriate administration set (not shown) that has been interconnected with outlet port 90 (FIG. 16).

Figure 18:
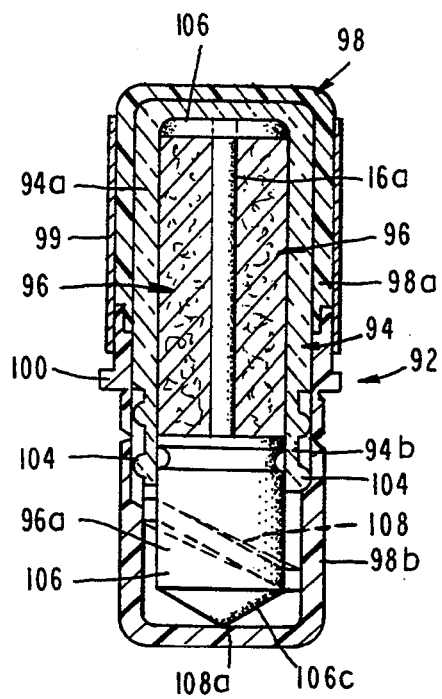
FIG. 18 is a cross-sectional view of still another form of the container, such as a glass vial, which contains the first component to be mixed.
Figure 19:
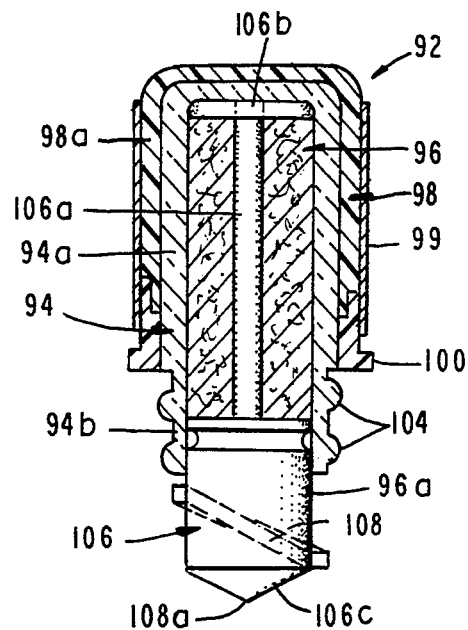
FIG. 19 is a cross-sectional view similar to FIG. 18 but showing the appearance of the container after the sealing cap has been removed.
Figure 20:
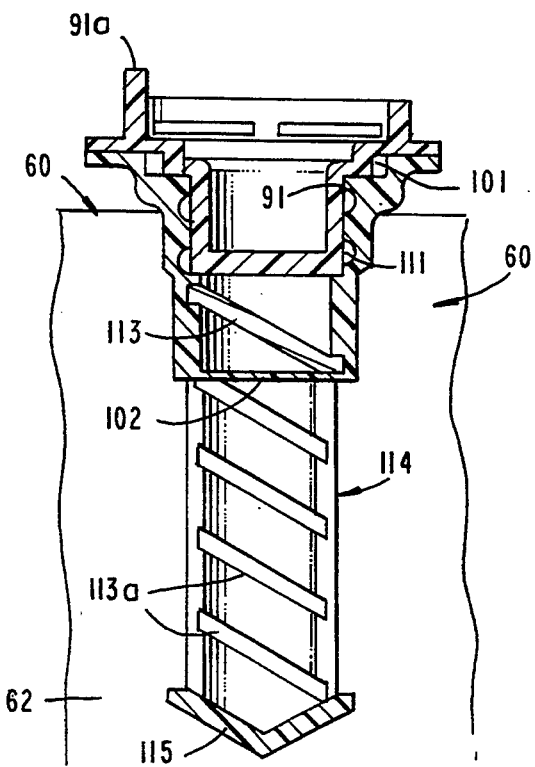
FIG. 20 is a fragmentary, cross-sectional view of still another form of the second container of the apparatus, such as a flexible bag, illustrating the construction of the mixing chamber.
Figure 21:
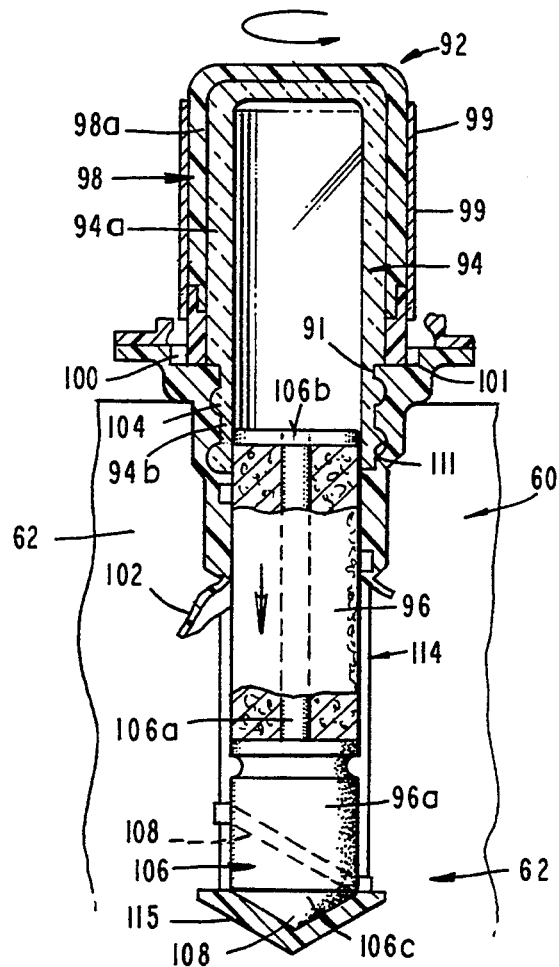
FIG. 21 is a fragmentary cross-sectional view illustrating the mating of the container containing the first component with the container containing the second component.

Turning to FIGS. 18 through 21 still another form of the apparatus of the invention for controllably intermixing the first component with the second liquid component is there shown. This embodiment is similar to the previously discussed embodiment and like numbers are used to identify like components. This latest embodiment also comprises a flexible container 60 having a fluid reservoir portion 62 for containing the second component (FIGS. 20 and 21). Container 60 also has an opening or inlet port 91 provided at the top of the bag and extending generally perpendicular to the top edge thereof. Inlet port 91 is sealed by a tearaway closure 91a which is readily removable as before. Port 91 is in fluid communication with reservoir portion 62 and, in a manner presently to be described, the container assembly of this later form of the invention is movable directly into the reservoir for component mixing.

As best seen in FIG. 18, the container assembly 92 of this embodiment of the invention comprises a glass vial 94 which carries within its internal chamber a functional support assembly 96. Vial 94 is surrounded by a two part protective covering 98 which includes a body portion 98a which encapsulates the non-threaded body portion 94a of the glass vial and a cover 98b which sealably encapsulates the threaded, open end 94b of the glass vial. Circumscribing cover 98 is a medicament primary label 99. As before, covering 98 includes an enlarged diameter portion having teeth 100 which irreversibly engage an annular female spline 101.

Protective cover 98b comprises a tear-off type cover which, as before, can be removed from the glass vial assembly by pulling on a tear tab. In this latter form of the invention, the opening, or inlet port, of the mixing chamber portion of the flexible container is initially sealed by a frangible membrane 102 of the type illustrated in FIG. 20.

Referring to FIG. 19 it can be seen that after tear-off cover 98b is removed from the vial assembly, external threads 104 which are provided on glass vial 94, are exposed. Similarly, the downwardly extending, or outboard extremity 96a of support assembly 96 is exposed. The outboard end 96a of support 96 is here provided in the form of an elastomers stopper like member 106 which is sealably received within the open end of glass vial 94 in the manner shown in FIG. 19. Member 106 includes a support means here shown as an outwardly extending column 106a terminating in an annular retention collar 106b. The end 106c of stopper 106 comprises a generally conically shaped portion having a membrane piercing point 108a. As best seen in FIG. 19, the body of the stopper is provided with a thread 108.

The inlet port assembly of this form of the invention is provided with two sets of internal threads which cooperate with threads 104 and with thread 108 in a manner presently to be described. More particularly, as best seen in FIG. 20, the inlet port includes a neck-like portion having threads 111 which cooperate with threads 104 of the glass vial. The neck like portion also includes a sleeve-like member 114 having a neck portion with a coarse thread 113 and a body portion having mating threads 113a. Threads 113 and 113a cooperate with thread 108 of stopper 106.

In using the apparatus of this second form of the invention, the tear cap is first removed from the vial assembly and the flex bag port cover or cap 91a is removed from the inlet port 91 of the flexible bag assembly 60 so as to expose the vertically extending mouth of the port. As indicated in FIG. 20, membrane 102 is positioned within the outboard end of the inlet port and, until ruptured, functions to sealably close the port to atmosphere.

Turning particularly to FIGS. 20 and 21, mating of the container assembly 92 with the flex bag assembly is accomplished as before by inserting the outboard, or threaded end of the glass vial 98 into port 91. Upon insertion of the container assembly into the connector port, threads 104 will mate and seal with first internal thread 111 provided in the inlet port assembly and thread 108 will mate with thread 113 provided in the neck portion of sleeve 114. As the forward end of the stopper 106 moves into the mixing chamber, point 108a will rupture frangible membrane 102 and continued rotation of the container assembly will cause the component parts of the assembly to move downwardly into reservoir 62 in the manner shown in FIG. 21. More particularly, threads 104 which are provided on the glass vial will advance within internal threads 111 provided proximate the inlet port or connector port of flex bag assembly. At the same time, thread 108 will mate with threads 113 and 113a causing support structure 96 and stopper 106 to move out of the open end of the glass vial and travel rapidly downwardly into reservoir 62. As the support structure assembly advances into the mixing chamber, support 96 will move telescopically outwardly of the internal chamber of the glass vial and stopper 106 will pierce frangible membrane 102. Continued rotation of the glass vial assembly 98 will cause downward extension of the support assembly until teeth 100 engage spline 101 and stopper 106 engages stop 115 which is located at the inboard terminus of sleeve 114.

With support 96 depending into reservoir 62 in the manner shown in FIG. 21, manual manipulation of the side walls of the reservoir portion of the flexible bag will cause the fluid within the reservoir, such as a diluent or other parenteral fluid, to flow around, about and through functional support 96 in a manner to expeditiously separate release remove the additive from the support and thoroughly intermix it with the liquid.

After the first and second components have been mixed and the solution thus formed can be withdrawn from the flex bag through an appropriate administration set (not shown).

Figure 22:
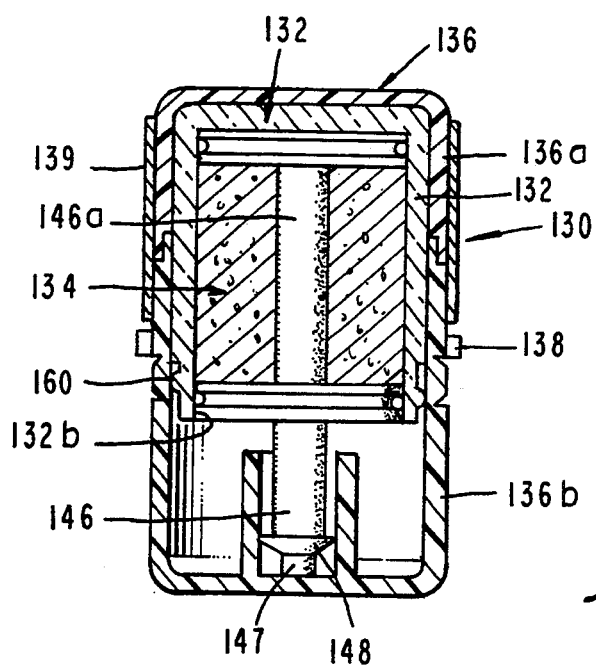
FIG. 22 is a cross-sectional view of yet another form of the container, such as a glass vial, which contains the first component to be mixed.
Figure 23:
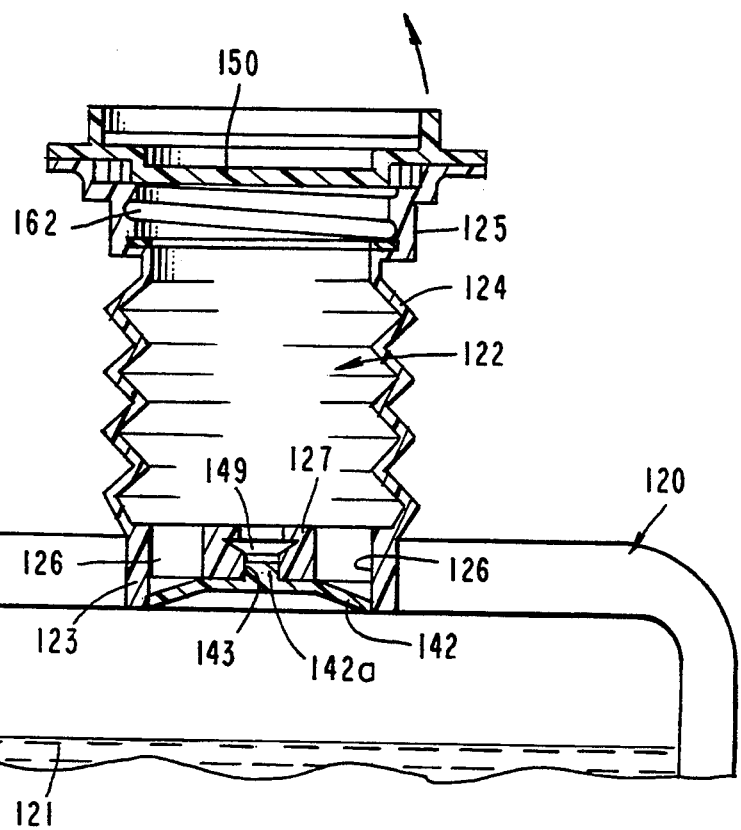
FIG. 23 is a fragmentary, cross-sectional view of yet another form of the second container of the apparatus, such as a flexible bag, illustrating the construction of the mixing chamber which, in this instance, comprises a bellows-like structure.

Turning to FIGS. 22 through 25 still another form of the apparatus of the invention for controllably intermixing the first component with the second liquid component is there shown. This embodiment comprises a container 120 having a fluid reservoir portion 121 for containing the second component (FIG. 23). Container 120 is provided with a uniquely configured, outwardly extending mixing chamber 122, formed by a bellows-like, collapsible wall 124 (see FIGS. 23 and 25) which depends from an upper, connector collar 125. The lower end of wall 124 terminates in a cylindrically-shaped collar 123 which is connected to the upper end of the flex bag. Chamber 122 is in fluid communication with the reservoir portion of the container via fluid passageways 126 provided in a transverse wall 127 which extends across collar 128. Once again, as indicated in FIG. 23, the mixing chamber extends generally perpendicular to, rather than parallel with, top and bottom edges of the container 120.

As best seen in FIG. 22, the container assembly 130 of this embodiment of the invention comprises a glass vial 132 which carries within its internal chamber a support assembly 134. Vial 132 is surrounded by a protective covering 136 which includes a body portion 136a which encapsulates the closed end portion 132a of the glass vial and a cover 136b which sealably encapsulates the open end 132b of the glass vial. Circumscribing cover 74 a medicament primary label 139. Cover 136 includes an enlarged diameter portion 138 having locking teeth 139, the purpose of which will presently be described. Protective cover 136b comprises a tear-off type cover which, as before, can be readily removed from the glass vial assembly.

Fluid passageways 126 which are provided in transverse wall 127 are initially sealed by a disc shaped elastomeric or plastic member 142 of the configuration shown in FIG. 23. Member 142 had a central protuberance 142a which is frictionally received within an aperture 143 provided in wall section 12. In a manner presently to be described, fluid passageways 126 can be opened for fluid flow by pushing downwardly on protuberance 142a of disc 142 with sufficient force to free it from aperture 143 and to cause it to separate from wall section 127 in the manner illustrated in FIG. 24.

Figure 24:
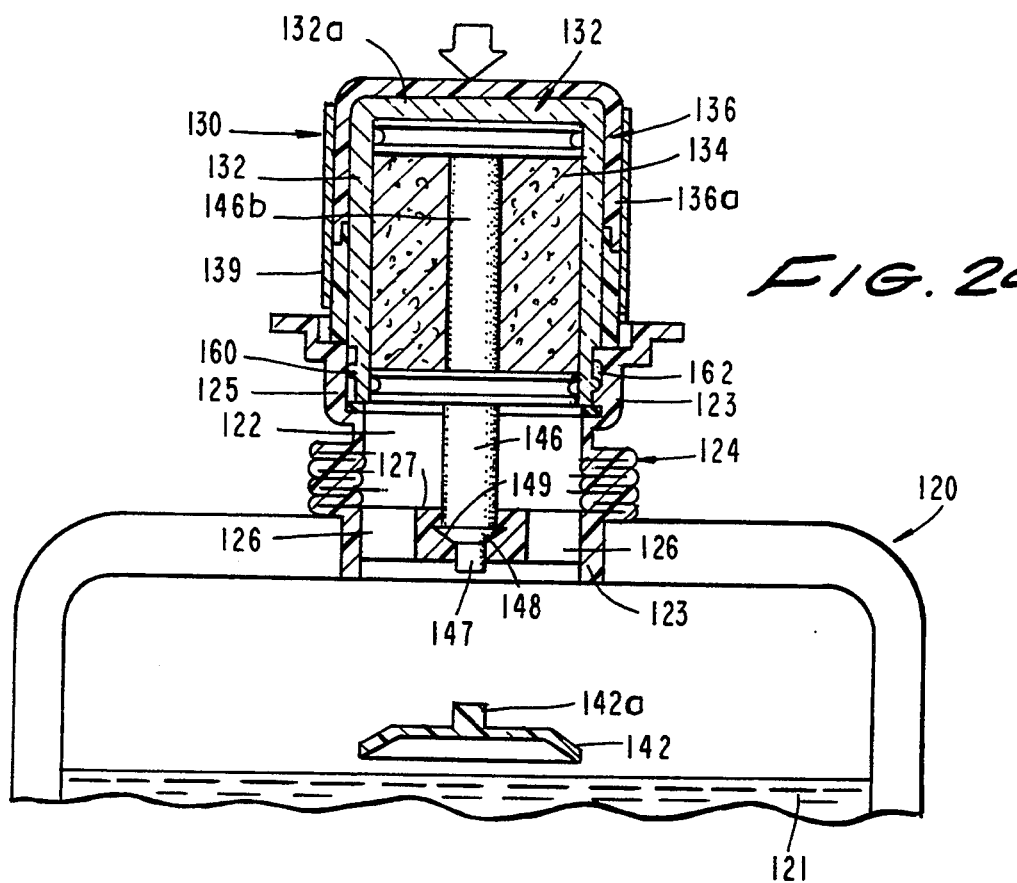
FIG. 24 is a fragmentary cross-sectional view showing the first container or glass vial assembly initially mated with the second container and with the bellows-like structure compressed.

Referring particularly to FIG. 24 it can be seen that after the tear-off cover is removed from the vial assembly, a depending column 146 is exposed. Column 146 is an extension of a central column 146a which forms a central core of cylindrically shaped functional support assembly 134. Provided at the lower extremity of column 146 is a disc engaging means 147 which is adapted to engage protuberance 142a of the sealing disc. Also provided proximate the lower end of the column is a locking means, shown here as a generally umbrella-shaped segment 148, which is lockably received within a cavity 149 provided in wall section 127.

In using the apparatus of this latest form of the invention, tear cap 136b is first removed from the vial assembly and the flex bag port cover or cap 150 (FIG. 23) is removed from the inlet connector collar 125 of the flexible container so as to expose the vertically extending mouth of the mixing chamber. As indicated in FIG. 23, sealing disc 142 is initially connected to wall 127 and functions to sealably close passageways 126 until the container assembly 130 can be mated with the flex bag assembly.

Turning to FIG. 24, mating of the container assembly 130 with the flex bag assembly is accomplished by inserting the outboard, or threaded end of the container assembly into connector port 125. Upon insertion of the container assembly into the connector port, external threads 160 provided on the glass vial will mate with internal threads 162 formed in connector collar 125 so that rotation of the vial will threadably interconnect the vial with the connector collar. As the container assembly is threadably received into and sealed with the connector port, column 146 will enter the bellows 124 and its lower extremity will engage protuberance 143 of disc 142. A downward force exerted on the container assembly will cause the bellows to collapse from the first position shown in FIG. 23 to the second position shown in FIG. 24. As the bellows-like wall is compressed column 146 will move downwardly forcing disc 142 to separate from wall 127 thereby opening fluid passageways 126. As the disc is separated, umbrella-like segment 148 of column 146 will enter into locking engagement with the appropriately shaped locking cavity 149 formed in wall 127 thereby interlocking together support assembly 132 and wall 127.

Figure 25:
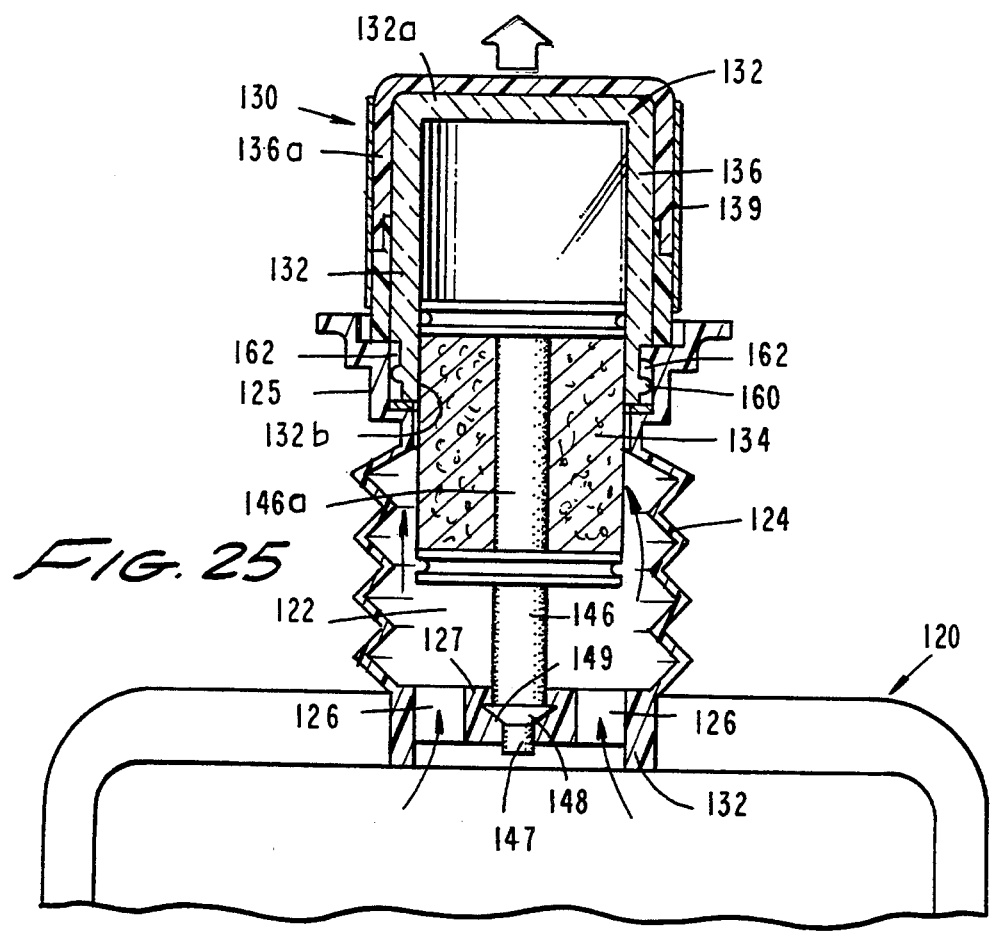
FIG. 25 is a view similar to FIG. 24 but showing the bellows-like structure expanded to permit intermixing of the first and second components.

With the container assembly threadably secured within the mouth of the flexible container, relaxation of the downward pressure being exerted on the container assembly will cause bellows 124 to return to the expanded position shown in FIG. 25. As the bellows expands, support 134 will simultaneously move telescopically outwardly of vial 132 and into open communication with the interior of mixing chamber 122. Upon inversion of the flexible container to insure contact with the reservoir contents, the bellows expansion will cause the fluid within the reservoir, such as a diluent or other parenteral fluid, to flow rapidly into mixing chamber 122 via passageways 126 and to rapidly move around, about and through functional support means 134. As the fluid moves around and through the support, additive will be expeditiously separated, released and substantially removed from the support and thoroughly intermixed with the liquid in reservoir 121.

After the first and second components have been mixed and the solution thus formed has returned to the reservoir of the flex bag, the solution can be withdrawn therefrom through an appropriate administration set (not shown).

Various forms of adding means and additive assemblies of the character illustrated in FIG. 17 can be used with each of the previously described embodiments. For example, the assemblies can comprise a porous substrate with interconnecting voids that include porous channels in its substructure which can extend completely throughout the substructure layer forming micro- and macro-pores on the surface and in the substructure. The substrate can comprise a crystal sponge 172 over which various outer coatings, 172b of one or more additives are bonded. Particularly useful in the form of the invention shown in FIG. 16 when the bottom wall of the mixing chamber is open, is a solid tubular member such as member 174 which has an internal, axially extending fluid passageway 174a, the inner wall of which, along with the outer wall of the tubular member, is lined with a separation coating or surface active agent or intermediate matrix affixing the additives such as medicaments, drugs and other beneficial agents can be used.

Still another form of additive assembly is of the character identified in FIG. 17 by the numeral 176. This assembly comprises a cylindrical member made up of a multiplicity of fused together microspheres 176a, each of which is coated with a surface active agent separation coating upon which is deposited and chemically anchored a biologically active material or other beneficial agent.

The additive assembly 178 of FIG. 17 comprises a cylindrically shaped structure made up of a plurality of interconnected bundles 178a the exposed surfaces of which carry the selected additive which has been removably interconnected thereto as a coating, vapor deposition or other chemical attachment.

Still another additive assembly 180 comprises a cylindrically shaped porous structure which is provided with pores 180a of varying sizes only some of which are coated, plugged or impregnated with selected additives and as necessary functional, intermediate materials. In some instances the plugging additives may comprise a grouping of micro capsules which may be of uniform content or mixed content. The micro capsules internally contain appropriate beneficial agents which are released upon disintegration of the micro capsule shell wall as a result of contact with the second component such as an aqueous solvent.

Another slightly more complex additive assembly is identified by the numeral 182. This assembly is made up of a plurality of spaced apart, porous disc shaped wafers 182a, 182b, 182c and 182d, each wafer being of the same or different construction, porosity and interconnecting voids and each having a multiplicity of reactive sites presenting to the liquid flow specially selected individual species of additives such as beneficial agents, elements or compounds so that multiple reactivities, and selectivities and sequential separations can be achieved. With this construction, a wide variety of liquid flow rates, and complex sequential separations and priority staged substance introduction into the system reservoir can be achieved by specially designing each of the wafers having unique affinity attachment and separation characteristics that cooperate to make up the functional structural support.

The numeral 184 of FIG. 17 identifies yet another form of the additive means of the invention. In this form of the invention, a generally cylindrically shaped functional support means is formed from a multiplicity of reactive sites 184a.

Still another form of the additive assembly is identified in FIG. 17 by the numeral 186. This micro-particulate assembly comprises a cylindrical, porous plug like substrate having a multiplicity of deposition sites which are coated with a separation or reactive coating upon which is deposited an additive such as a biologically active material or other beneficial agent.

The base materials for the substrates can include ceramics, carbon composites, cellulose derivatives, polymers, and a wide variety of other materials.

Figure 26:
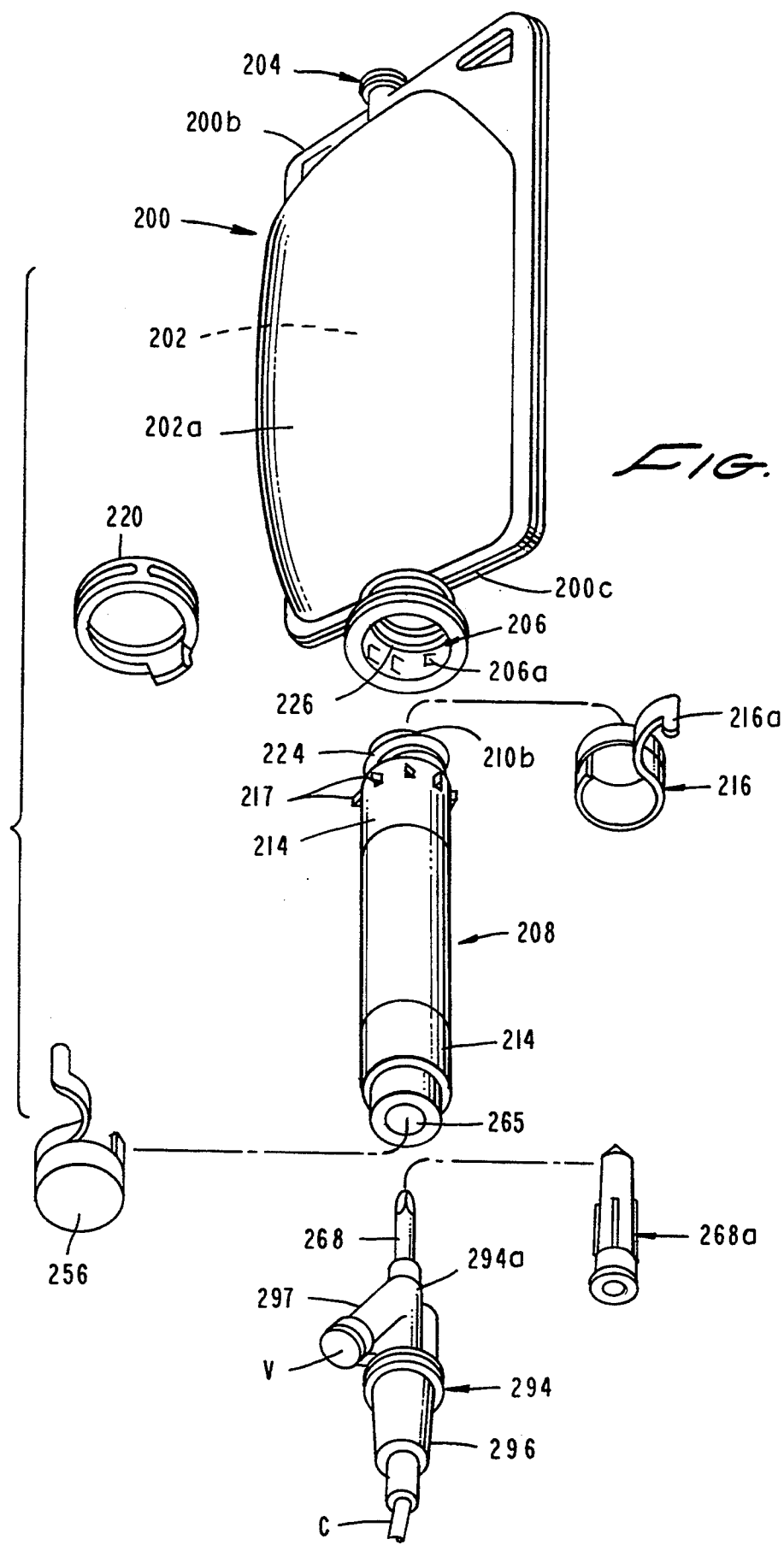
FIG. 26 is a generally perspective, exploded view of another form of the mixing and delivery system of the present invention.

Referring now to FIGS. 26 through 32 and particularly to FIG. 26, yet another form of the apparatus of the invention for controllably intermixing the first component and the second liquid component is there shown. This embodiment is similar to the previously discussed embodiment save that the container or vial containing the first component is disposed in the outlet passageway of the container containing the second component. This embodiment comprises a flexible container 200 having a fluid reservoir portion 202 with flexible side walls 202a for containing the second component. Container 200 is provided with an upper inlet port 204 and a lower outlet port assembly 206. In this later form of the invention, it is to be observed that outlet port assembly 206 is mateable with container assembly 208 which contains the first component and which extends generally perpendicular to top and bottom edges 200b and 200c.

As best seen by also referring to FIG. 30, the container assembly 208 of this embodiment of the invention comprises a glass vial 210 which carries within its internal chamber 211 a unique additive support 212, or additive presentation means, the details of which will be described hereinafter. Vial 210 is surrounded by a plastic overcover sheath 214 which includes a body portion 214a which encapsulates the non-threaded body portion 210a of the glass vial. A tear away plastic cap 216 sealably encapsulates the threaded, open end 210b of the glass vial (FIG. 26). Circumscribing the upper portion of sheath 214 are circumferentially spaced locking teeth 217 of the character previously described and as shown in FIG. 1 for locking the container assembly to the flexible bag.

Tear-off type cap 216 can be removed from the glass vial assembly by pulling on a tear tab 216a (FIG. 26). Similarly, the lower opening, or outlet port 206 of the flexible container is initially sealed by a sterile tear-off cap 220 of the type illustrated in FIG. 26 and of a character well known in the art.

Referring to FIG. 26 it can be seen that after tear-off cover portion 216 is removed from the vial assembly, external threads 224 which are provided on glass vial 210, are exposed. Outlet port assembly 206 of container 200 is provided with internal threads 226 which cooperate with threads 224 in the manner shown in FIG. 30.

Figure 27:
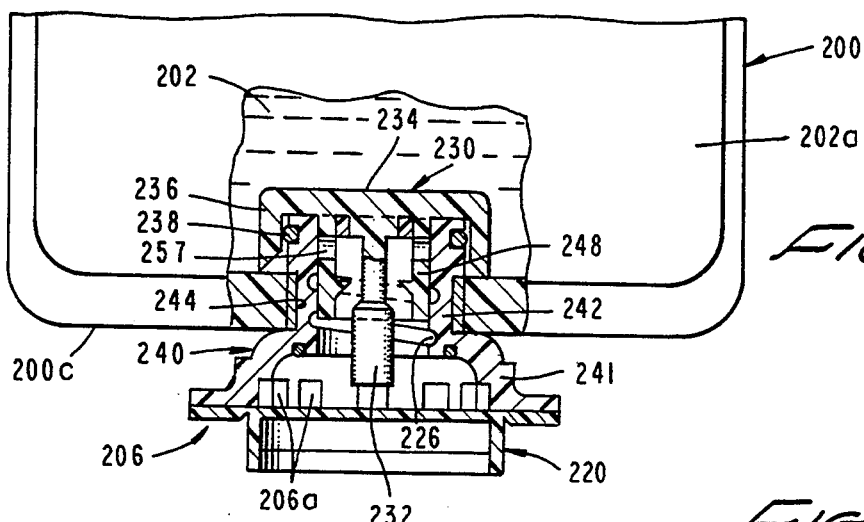
FIG. 27 is an enlarged fragmentary, cross-sectional view of the lower portion of the flex bag shown in FIG. 26.

As best seen in FIG. 27, outlet port assembly 206 of container 200 is provided with first flow control means for controlling fluid flow outwardly of the outlet port. The first flow control means is here provided as a cap-like closure member 230 having a central downwardly extending pusher member or pintle 232 which is integrally formed with a top wall 234. Circumscribing top wall 234 is a downwardly depending skirt 236 which is normally in sealing engagement with an elastomeric O-ring 238 provided on a housing assembly 240 which also comprises a part of the first flow control means.

Housing assembly 240 includes a bell-like portion 241 and an integral neck portion 242 which is sealably received within an opening 244 provided in bottom wall 200c of the container 200. The previously mentioned internal threads 226 are provided internally of neck portion 242 and are adapted to mateably receive threads 224 on container assembly 208 when the first and second containers are mated in the manner shown in FIG. 30. Neck portion 242 is also sized to telescopically receive a downwardly depending cylindrical extension 248 which is integrally formed with top wall 234 of closure member 230.

Figures 28, 29:
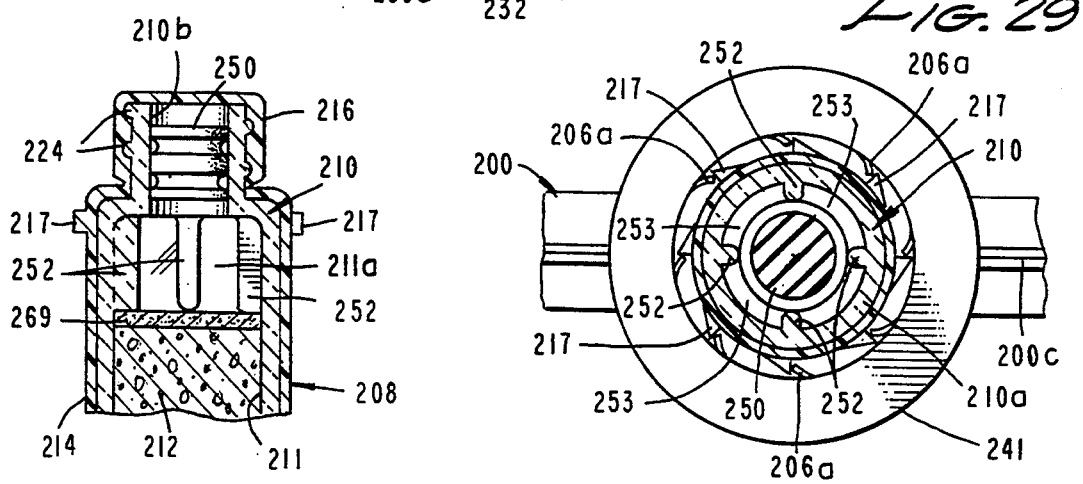
FIG. 28 is a fragmentary, cross-sectional view of the upper portion of the container shown in FIG. 26 which contains the first component to be intermixed with the second component contained within the flex bag.
FIG. 29 is a cross-sectional view taken along lines 29—29 of FIG. 30.

Turning to FIG. 28, the open end 210b of vial 210 is normally closed by second flow control means which functions to control fluid flow into chamber 211 of the vial which contains support 212. The second flow control means is here provided as an elastomeric closure plug 250, which, in a manner presently to be described, is engageable by pintle 232 of closure member 230.

Disposed below plug 250 is a hollow chamber portion 211a within which is provided circumferentially spaced ribs 252 which function to hold plug 250 in position within chamber 211a. Ribs 252 are integrally formed with glass vial 210 (FIG. 29) and function to define fluid flow passageways 253 which permit fluid flow around plug 250 when the plug has been moved into chamber 211a.

Figure 30:
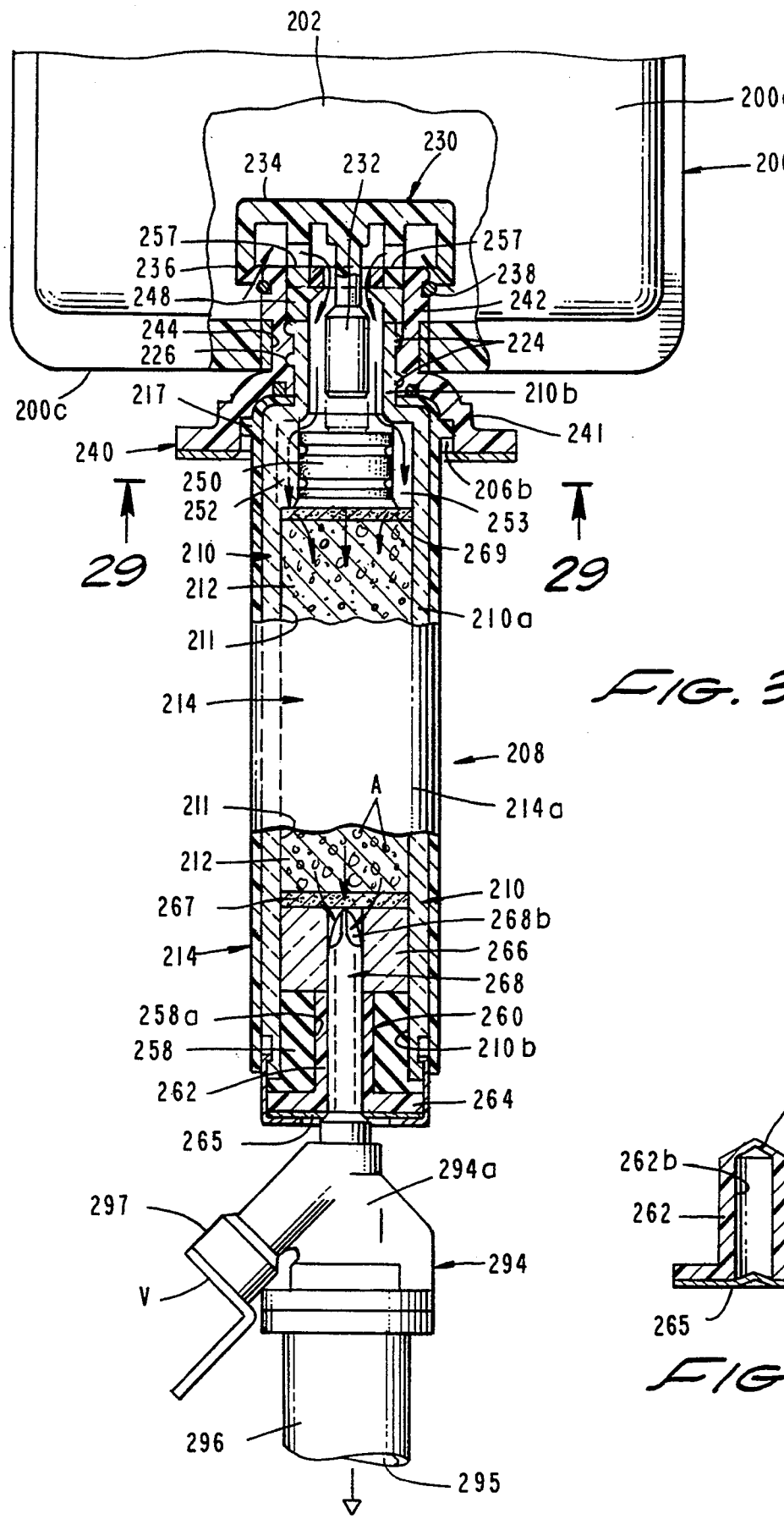
FIG. 30 is a fragmentary view partly in section illustrating the manner in which the container containing the first component is interconnected with the second container containing the second component.
Figure 31:
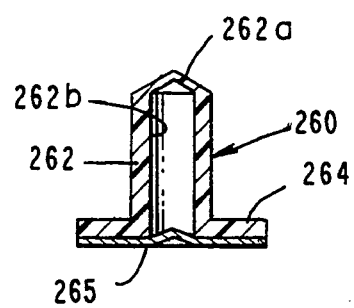
FIG. 31 is a fragmentary, cross-sectional view of the spike port which comprises a part of the container containing the first component.
Figure 34:
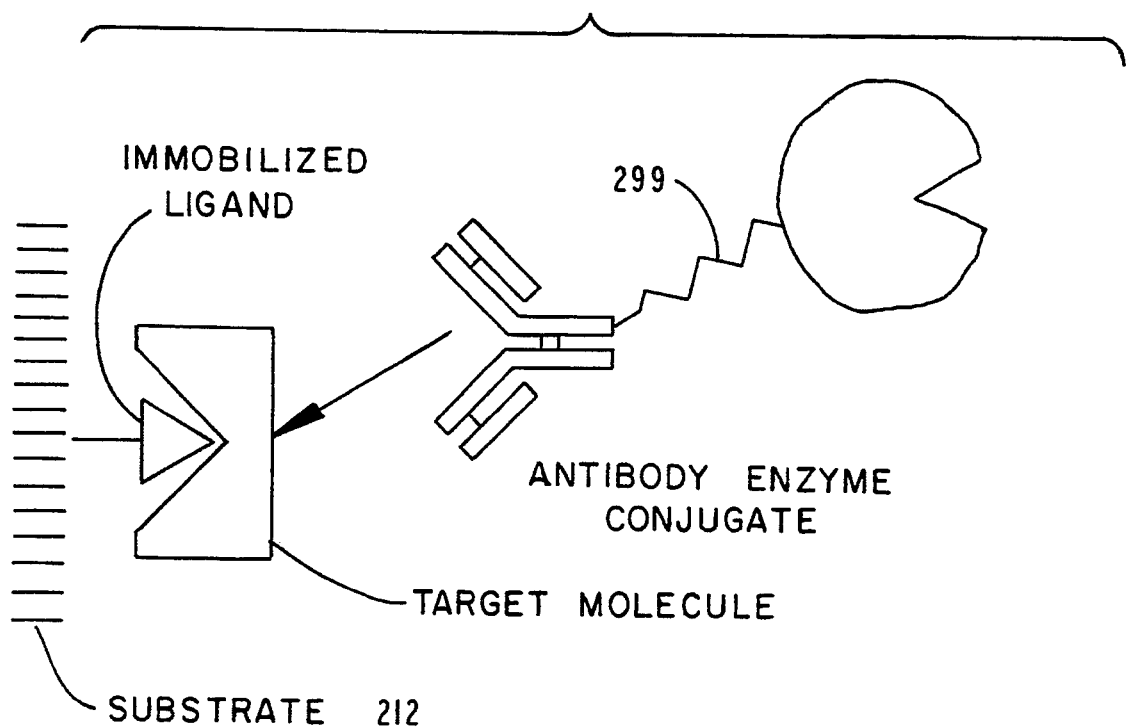
Figure 35:
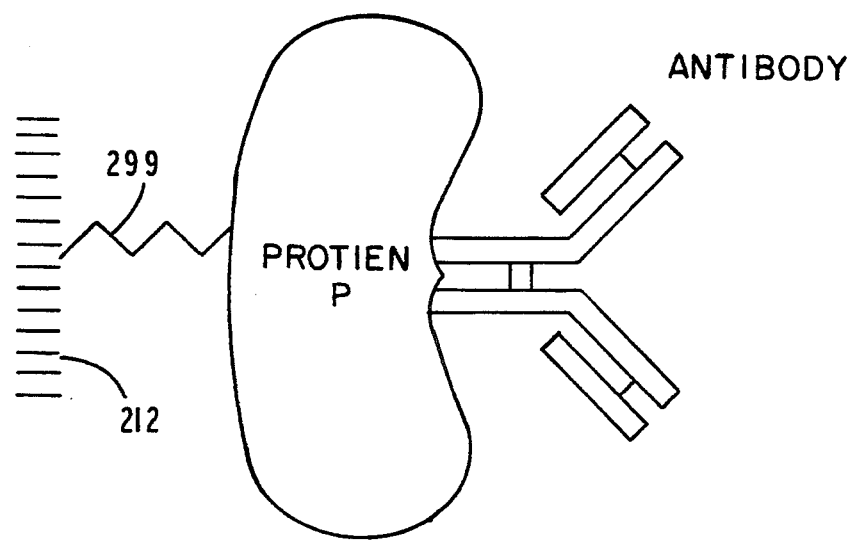

Referring to FIGS. 26 and 30, the bottom end of assembly 208 is normally closed by tear-away cap 256. A cylindrically shaped rubber filler plug 258 is sealably received within opening 210b of glass vial 210. Plug 258, as well as a spike port assembly 260 which is receivable within central opening 258a of plug 258, form a port of the third flow control means of the invention for controlling fluid flow outwardly of vial assembly 210. As indicated in FIG. 31, spike port assembly 260 includes a hollow body portion 262 and a flange portion 264. Body portion 262 is closed by a pierceable end wall 262a and a pierceable membrane 265 is bonded to flange 264 to close the central bore 262b of body 262. Body 262 and membrane 265 can be constructed from polyvinal chloride or any other suitable material.

Disposed between the bottom end of additive support 212 and plug 258 is a polymer distribution plug 266 for regulating fluid flow outwardly of vial 210. Distribution plug 266 has a central bore which is adapted to closely receive the delivery spike 268 of the delivery means of the invention which will presently be described. A lower glass frit 267 is provided between plug 266 and support 212 and an upper glass frit 269 is provided between the upper end of support 212 and ribs 252. The additive A which is removably connected to support 212 is, therefore, sandwiched between frits 267 and 269 so that liquids flowing through the glass vial will flow through the glass frits.

In using the apparatus of this latest form of the invention, tear cap 216 is first removed from the vial assembly and the flex bag port cover or cap 220 is removed from the outlet port of the flexible bag assembly 200 so as to expose the vertically extending mouth of the port in the manner illustrated in FIG. 26. Mating of container assembly 208 with the flex bag assembly 200 is then accomplished by inserting the outboard, or threaded end of the glass vial 210 into bell shaped portion 241 of the flex bag assembly. Upon insertion of the container assembly into portion 241, threads 224 will mate with the internal threads 226 and the open upper end 210a of the vial will move into position to receive the lower end of pintle 232. Continued rotation of the vial assembly will cause the pintle to push plug 250 downwardly from the first position shown in FIG. 28 into the second position shown in FIG. 30 where the plug has seated within chamber 211a in the manner shown in FIG. 30. Plug 250 is constructed so that upon entering chamber 211a, it will expand to a diameter sufficient to prevent it from reseating within opening 210a. As plug 250 moves downwardly, cap assembly 230 will move upwardly from the first position shown in FIG. 27 to the second position shown in FIG. 30. In this second position, skirt 236 will move clear of O-ring 238 permitting fluid contained within the flex bag to flow into passageways 257 provided in cylindrical portion 248 and then downwardly into vial 210 in the manner shown by the arrows in FIG. 30. The fluid will then flow through glass frit 269, around, about and through the substrate in a manner to remove the additive therefrom by one or more of the previously described mechanisms. It should also be noted that as the upper end of the vial moves into threaded engagement with the flex bag outlet port, the locking teeth 217 provided on plastic cover 214 will lockably engage locking tabs 206a provided on the inner wall of bell shaped portion 241 of the flex bag assembly thereby irreversibly locking the vial assembly and the flex bag assembly together (FIGS. 29 and 30).

Figure 32:
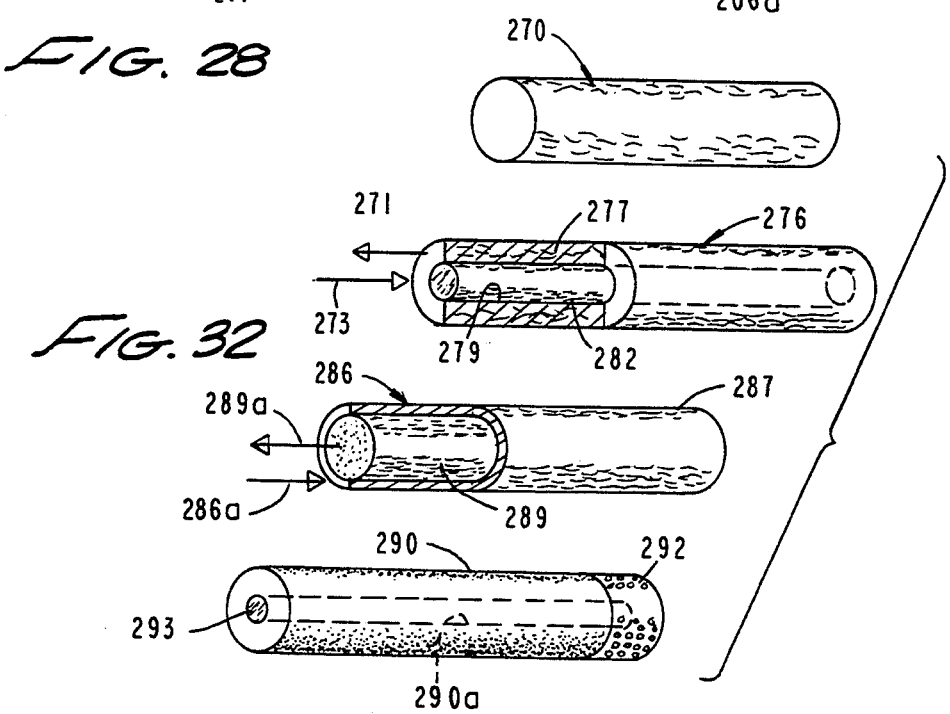
FIG. 32 is a generally perspective view of the various additional substrate constructions of the invention.

Turning now to FIG. 32, various other forms of adding means of the invention, in addition to those shown in FIG. 17, are there illustrated. For example, numeral 270 identifies an assembly comprising a cylindrically shaped, porous synthetic support with interconnecting voids, which will permit liquid flow therethrough. Substrate 270 which can be constructed from polystyrene, is adapted to removably carry one or more of the additives previously identified. The selected additives such as elements, chemical compounds, drugs and functional intermediates can be removably attached to the substrate by various techniques well known to those skilled in the art. The additives which are removably affixed to the substrate are, of course, intermixed with the liquid component, such as a sterile diluent, as the diluent flows from the flex bag interiorly of glass vial 210.

Another form of additive assembly designated in FIG. 32 by the numeral 276, comprises an outer tubular porous hydrophylic substrate 277 having an axially extending bore 279 within which is received a cylindrically shaped hydrophobic substrate 282. The additives such as chemical compounds and beneficial agents, or medicaments are removably affixed to substrate 277 in the manner previously described herein. With the construction shown, gases can pass through substrate 282 only in the direction of arrow 273 and liquids can pass through substrate 277 only in the direction of arrow 271. In this way, airlock within the flex bag is effectively prevented in a manner which will hereafter be described.

Still another form of additive assembly is identified in FIG. 32 by the numeral 286. This assembly comprises a tubular, porous hydrophobic member 287 having a central bore within which is received a cylindrical, porous substrate 289. Substrate 289 provides a scaffold matrix for affinity attachment of additives of a character presently to be described. Member 287 functions to permit replacement gas flow toward the liquid reservoir of the flex bag in the direction of arrow 286a of FIG. 32. Fluid flow of the diluent is permitted in the direction of arrow 289a.

The numeral 290 of FIG. 32 identifies yet another form of the adding means of the invention. In this form of the invention, a generally cylindrically shaped functional support means for affinity attachment, and subsequent release of the additive, is formed from azalactone beads presenting a multiplicity of reactive sites over a wide area of species immobilization. In this form of the invention, flow rate control means in the form of a porous media 292 is affixed to one end of the substrate. Media 292 functions to control fluid flow toward the outlet of the vial assembly and to control residence time of the fluid within the substrate 290. A cylindrically shaped member 293, which is disposed within bore 290a, functions to permit venting gas to flow toward the flex bag.

Substrate matrices 270, 277, 289, and 290 can be constructed from a wide variety of materials including ceramics, glass, polymers, cellulose, polyacrylamide beads, polyacrylamide gels, dextron based gels, azlactone beads, and various other materials for synthetic supports of a character well known to those skilled in the art including biomosaic polymers.

Turning to FIGS. 26 and 30 the delivery means of the invention for delivery of the beneficial agent to the patient comprises a delivery spike assembly 294. This assembly is of a standard construction having the previously identified spike 268 over which a protective cover or cap 268a can be emplaced (FIG. 26). Spike 268 is connected to a housing 294a which has a fluid flow outlet 295 in communication with a drip chamber 296 which, in turn, is connected to a cannula C. A side arm 297 connected to housing 294a functions to provide vent means V for providing replacement air to the flex bag in a manner well understood by those skilled in the art.

In use, spike 268 of the spike assembly is inserted into a spike port 260 with sufficient force to pierce membrane 265 and end wall 262a in the manner shown in FIG. 30 so as to open fluid flow between distribution plug 266 and the interior fluid flow passageway 268b of the spike. Fluid flowing through the distribution plug enters the flow passageway of the spike, then flows into drip chamber 296 and then from the drip chamber into cannula C.

In this latest form of the invention, the additives which can be removably affixed to support 212 can take various forms and, as previously mentioned, can be removably affixed to the functional support means or support 212 in various ways to enable the use of conventional separation techniques as well as the use of separation techniques broadly defined by the term chromotography. Chromotography as used herein refers to a group of separation techniques which are characterized by a distribution of the molecules to be separated between two phases, one stationary and other mobile. Affinity chromatography involves the use of biological interactions and contemplates the use of affinity chromatography supports through which the eluting fluid flow. In the present embodiment of the invention, the additive presentation means assumes the character of an affinity chromatography support to which various ligands are attached. In the practice of affinity chromotography techniques, one of the members of the pair in the interaction, the ligand, is immobilized on a solid phase, while the other, the counterligand (most often a protein), is absorbed from the extract that is passing the substrate during the manufacturing process. Importantly, affinity chromatography techniques can include the use of a highly versatile azlactone functional compounds, such as azlactone functional beads, as well as the use of a wide variety of other media for activation and coupling chemistry. Examples of ligands that can be attached to the affinity supports include antibodies, enzymes, lectins, nucleic acids hormones and vitamins. Examples of important counterligands include antigens, virus, cells, cell surface receptors and the like. Chromotography and affinity chromatography techniques are described in detail in *Protein Purification* by Janson and Ryden, Copyright 1989 and reference should be made to his work to provide a working understanding of the techniques.

Polymeric azlactones are well known in the prior art. Their use in the production of homopolymers and copolymers has been described in a number of patents. See for example, U.S. Pat. No. 3,488,327 (issued Jan. 6, 1970 to F. Kollinsky et al.); U.S. Pat. No. 4,304,705 (issued Dec. 8, 1981 to S. M. Heilmann et al.); and U.S. Pat. No. 4,737,560 (issued Apr. 12, 1988 to S. M. Heilmann et al.); and U.S. Pat. No. 5,013,795 issued May 7, 1991 to Coleman, et al.

Azlactones, or oxazolones are cyclic anhydrides of N-acylamino acids and have been used extensively in organic synthesis. The formation of a five-member azlactone of particularly useful functionality for immobilization purposes can be accomplished through the reaction of a carboxylate group with a-methyl alanine using a two-step process. (See *Immobilized Affinity Ligand Techniques*-Hermanson, Mallia and Smith, Copyright 1992). One method of forming azlactone beads, the use of which has been previously mentioned herein, makes use of this process in the polymerization of monomers to first yield a carboxyl group on the matrix. In the second step, the azlactone ring is formed in anhydride, alkyl chloroformates, and carbondiimides. The process of forming these active groups and of making beaded polymeic supports containing the has been thoroughly described in patents assigned to 3M Corporation (U.S. Pat. Nos. 4,871,824 and 4,737,560). These support materials are not available under the tradenames "Emphasis". U.S. Pat. Nos. 5,045,615 and 5,013,795 which have been assigned to 3M Corporation also describe recent advances in this technology.

As pointed out in the 3M Corporation U.S. Pat. No. 4,737,560, azlactone-functional polymer beads are useful reactive supports for the attachment of functional materials to provide novel adduct beads. The adduct beads are useful as complexing agents, catalysts, reagents, and as enzyme or other protein-bearing supports. The term "support" or "affinity support" as used in this sense is usually understood to refer to a combination of (1) a ligand (usually of some known molecular configuration), that is firmly attached (e.g., immobilized), often by covalent means, and (2) a matrix (usually a solid insoluble substance). Azlactone support matrix materials and coupling chemistry is also of special interest because of its accessible matrix surface area and effective ligand diversity that can be attached to that surface.

U.S. Pat. No. 4,072,566 issued to Lynn on Feb. 7, 1978, and entitled "Immobilized Biologically Active Proteins" discloses a method of bonding enzymes or other biologically active proteins to an inorganic support material using p-phenylenediamine. The support materials disclosed as useful in the invention include siliceous materials, stannic oxide, titania, manganese dioxide, and zirconia.

The functional support structure 212 of the present embodiment of the invention can take on the character of an affinity support and as shown in FIGS. 33, 34, 35 and 36 is uniquely constructed to permit enzymes or other biologically active proteins to be bound thereto for later removal. This is accomplished by treating functional support 212 in the manner disclosed in the prior art patents identified in the preceding paragraphs with a compound having selective reactive functional groups such as azlactone functional compounds. In this way complexing agents, catalysts and biological materials such enzymes, proteins or other affinity absorbents, as well as biomacromolecules can be attached to the carrier for later removal and recovery.

When attaching certain biologically active proteins and other macro molecules, the use of spacer arms or leashes have been found to be very beneficial (see FIG. 33). Spacer arms or leashes 299 are low-molecular-weight molecules that are used as intermediary linkers between a support material and an affinity ligand L. Usually spacers consist of linear hydrocarbon chains with functionalities on both ends of each coupling to the support and ligand. First, one end of the spacer is attached chemically to the matrix using traditional immobilization chemistries and the other end is connected subsequently to the ligand using a secondary coupling procedure. The result is an immobilized ligand that sticks out from the matrix backbone by a distance equal to the length of the spacer arm chosen.

The principal advantage of using a spacer arm is that it provides ligand accessibility to the binding site S of a target molecule. When the target molecule is a protein with a binding site somewhat beneath its outer surface (upper portion of FIG. 33), a spacer is essential to extend the ligand out far enough from the matrix to allow interaction. When the ligand binding site is buried or is disposed in a pocket located just below the surface of the protein, a ligand that is either below the surface of the support material or a ligand that is attached directly to the surface cannot reach the level of the binding site on an approaching protein molecule. The result may be weakened interaction or no binding at all. Accordingly, in these instances, a spacer arm is required to provide the ligand accessibility to the binding site of the protein molecule. The details covering the use of spacer arms are fully set forth in Section 3.1.1 of the work entitled *Immobilized Affinity Ligand Techniques*. This Section 3.1.1 is incorporated herein by reference.

Figure 36:
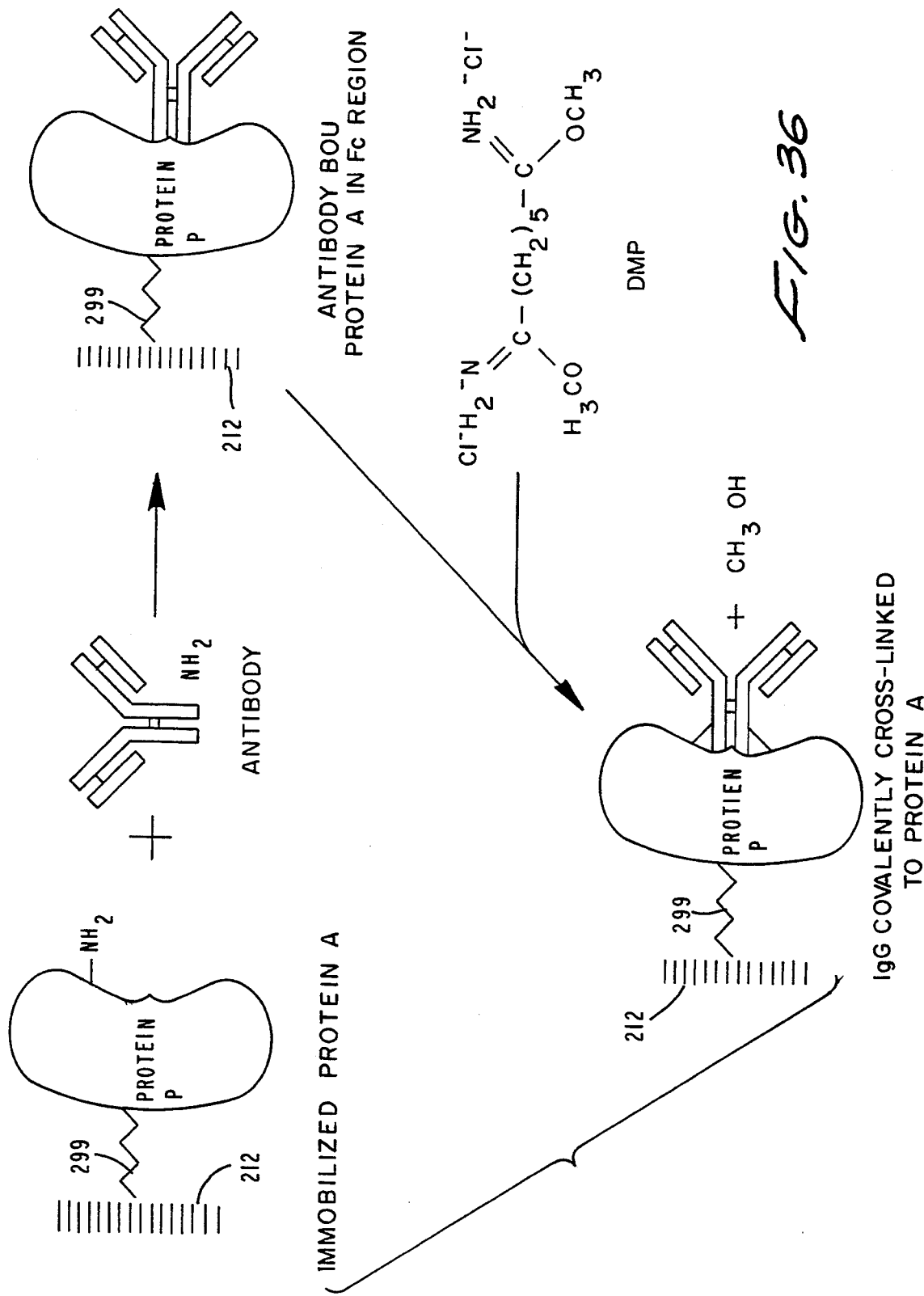

It is to be noted that an immobilized protein P can also be used to immobilize an antibody molecule (FIG. 35) by taking advantage of the natural affinity of the protein for immunoglobulins. Incubation of a specific antibody with the protein matrix will bind the antibody in the Fe region, away from the antigen binding sites (FIG. 36). Subsequent cross-linking of this complex with DMP (dimethyl pimelimidate) yields a covalently attached antibody with the antigen binding sites facing outward and free to interact with antigen.

With rigid support matrix materials, a spacer molecule may also provide greater flexibility, allowing the immobilized ligand to move into position to establish the correct binding orientation with a protein. The degrees of freedom that a hydrocarbon extender can provide are much greater than the movement possible within the polymeric backbone of a matrix.

The choice of spacer molecule can affect the relative hydrophilicity of the immediate environment of an immobilized ligand. Molecules containing long hydrocarbon chains may increase the potential for nonspecific hydrophobic interactions, especially when the affinity ligand is small and of low molecular weight. Selecting spacers that have more polar constituents, such as secondary amines, amide linkages, ether groups or hydroxyls will help keep hydrophobic effects at a minimum.

It is important to recognize that, as used in the present form of the invention, affinity supports are now capable of total binding capacity at a level that enables attachment to the support of additives in substantial amounts for subsequent release recovery and infusion of beneficial agents in a manner which can be therapeutically efficacious to a patient. Alternate disassociation constants for desorption of the absorbed component from the affinity matrix can be established so as to critically determine the optimal conditions for elution of the bound additives over time. The elution diluent acts as the desorption agent when exposure of the elution agent to the substrate breaks the affinity attachment bond as a function of time.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for controllably intermixing a first component and a second liquid component comprising:
   (a) a first container having a fluid reservoir for containing the second component and an outlet assembly having a fluid outlet in fluid communication with said fluid reservoir and first flow control means for normally closing said fluid outlet, said first flow control means being movable into a fluid outlet opening position;
   (b) adding means for presenting the first component to the second component for intermixing therewith, comprising:
      (i) a support upon which the first component is removably affixed;
      (ii) a second container for containing said support, said second container having a plug receiving chamber; and
      (iii) connector means for directly connecting said second container to said outlet assembly of said first container so that said support can be exposed to fluid flowing out of said fluid outlet of said container; and
   (c) second flow control means for controlling the flow of fluid into said second container, said second flow control means comprising a closure plug engageable by said first flow control means as said second container is connected to said outlet assembly, to move said closure plug into said plug receiving chamber and simultaneously to move said first flow control means into said fluid outlet opening position whereby fluid can flow toward said adding means.

2. An apparatus as defined in claim 1 in which said first component comprises a beneficial agent and in which said second component comprises a parenteral fluid.

3. An apparatus as defined in claim 1 in which said first component comprises a drug and in which said second component comprises a diluent.

4. An apparatus as defined in claim 1 in which said first component comprises a biologically active material.

5. An apparatus as defined in claim 1 in which said first component is removable from said support using affinity chromotography techniques.

6. An apparatus as defined in claim 5 in which said first component is connected to said support using azlactone functional compounds.

7. An apparatus as defined in claim 6 in which said first component comprises a protein.

8. An apparatus for controllably intermixing a first component and a second liquid component comprising:
   (a) a flexible container having a fluid reservoir for containing the second liquid component and a fluid outlet assembly having a fluid outlet having first threads said fluid outlet being in fluid communication with said fluid reservoir and first flow control means for controlling fluid flow through said fluid outlet, said first flow control means comprising a closure assembly having a closure cap for closing said fluid outlet and a pintle connected to said closure cap, said closure cap being movable from a first fluid outlet closing position to a second fluid outlet opening position;
   (b) adding means for presenting the first component to the second component for intermixing therewith, comprising:
      (i) a support upon which the first component is removably affixed;
      (ii) a vial for containing said support said vial having second threads mateable with said first threads and a plug receiving chamber; and
      (iii) connector means for directly connecting said vial to said fluid outlet assembly of said flexible container so that said support is exposed to fluid flowing through said fluid outlet, said connector means comprising threads provided on said vial for threadable interconnection with threads provided proximate said fluid outlet of said flexible container;
   (c) second flow control means for controlling the flow of fluid into said vial, said second flow control means comprising a closure plug engageable by said pintle as said vial is connected to said fluid outlet assembly to move said closure plug from a first inlet closing position into an inlet opening position wherein said plug is moved into said plug receiving chamber and simultaneously to move said closure cap toward said second open position whereby the liquid contained within said flexible container can flow from said fluid reservoir into said vial containing said support.

9. An apparatus as defined in claim 8 in which said first component comprises a biologically active material.

10. An apparatus as defined in claim 8 in which said first component comprises a drug.

11. An apparatus as defined in claim 8 in which said second component comprises a diluent.

12. An apparatus for controllably intermixing a first component and a second liquid component comprising:
   (a) a flexible container having top, bottom and side portions and including a fluid reservoir for containing the second component and a fluid outlet assembly connected to said bottom portion having a fluid outlet in fluid communication with said fluid reservoir, said fluid outlet assembly having internal threads and first flow control means for controlling fluid flow through said fluid outlet;
   (b) adding means for presenting the first component to the second liquid component for intermixing therewith, comprising:
      (i) a vial including an internal chamber having a fluid inlet and being provided with external threads mateable with said internal threads of said fluid outlet assembly, said vial having second flow control means for controlling the flow of liquid into said internal chamber, said second flow control means being operable by said first flow control means of said fluid outlet assembly; and
      (ii) adding means contained within said internal chamber said adding means comprising said first component and a presentation means for presenting said first component to said second component as said second component flows through said internal chamber, said presentation means comprising a porous support said first component being immobilized on said porous support and is removable therefrom using affinity chromotography techniques.

13. A device as defined in claim 12 in which a ligand is connected to said support and a target molecule is connected to said ligand.

14. A device as defined in claim 13 in which a spacer arm is connected to said support and in which a ligand is connected to said spacer arm.

15. A device as defined in claim 14 in which an enzyme is connected to said target molecule.

16. A device as defined in claim 15 in which said target molecule is a protein.

17. An apparatus as defined in claim 16 in which said first flow control means comprises a closure cap for closing said fluid outlet and a pintle connected to said closure cap.

18. An apparatus as defined in claim 17 in which said second flow control means comprises a closure plug for closing said fluid inlet of said internal chamber, said closure plug being engagable by said pintle to move said closure plug from a first inlet closing position to a second inlet opening position wherein said closure plug is disposed within said internal chamber of said vial.

19. An apparatus as defined in claim 18 in which said vial is provided with a fluid outlet having third closure means for closing said fluid outlet.

20. An apparatus as defined in claim 19 in which said third closure means comprises a pierceable membrane closing said fluid outlet.

21. An apparatus as defined in claim 20 further including delivery means for delivering the intermixed first and second components to a patient, said delivery means comprising delivery spike assembly having a spike provided with a fluid passageway and a cannula connected to said spike, said spike being adapted to penetrate said pierceable membrane whereby the intermixed first and second components can flow from said internal chamber of said vial into said fluid passageway of said spike.

22. An apparatus for controllably intermixing a first component and a second liquid component comprising:
(a) a container having a fluid reservoir for containing the second liquid component and a fluid outlet assembly having a fluid outlet in fluid communication with said fluid reservoir and first flow control means for controlling fluid flow through said fluid outlet, said first flow control means comprising closure means for normally closing said fluid outlet, said closure means being movable from a first fluid outlet closing position to a second fluid outlet opening position;
(b) adding means for presenting the first component to the second component for intermixing therewith, comprising:
 (i) a support upon which the first component is removably affixed;
 (ii) a vial for containing said support, said vial having a plug receiving chamber and being mateable with said fluid outlet assembly for moving said first flow control means toward said second fluid outlet opening position; and
 (iii) connector means for directly connecting said vial to said fluid outlet assembly of said flexible container so that said support can be exposed to fluid flowing through said fluid outlet; and
(c) second flow control means for controlling the flow of fluid into said vial, said second flow control means comprising a closure plug and cooperating with said first flow control means to move said closure plug from a first inlet closing position into an inlet opening position wherein said plug is moved into said plug receiving chamber of said vial as said first flow control means is moved toward said second fluid outlet opening position, whereby the liquid contained within said container can flow from said fluid reservoir into said vial container said support.

23. An apparatus as defined in claim 22 in which said first flow control means comprises a closure cap for closing said fluid outlet and a pintle connected to said closure cap, said closure plug being engageable by said pintle to move said closure plug from a first inlet closing position and into said plug receiving chamber of said vial.

24. An apparatus as defined in claim 22 in which said first component comprises a biologically active material.

25. An apparatus as defined in claim 22 in which said first component is removable from said support using affinity chromotography techniques.

26. An apparatus as defined in claim 25 in which said first component is connected to said support using azlactone functional compounds.

27. A device as defined in claim 26 in which a ligand is connected to said support and a target molecule is connected to said ligand.

28. A device as defined in claim 27 in which a spacer arm is connected to said support and in which a ligand is connected to said spacer arm.

29. A device as defined in claim 28 in which an enzyme is connected to said target molecule.

30. A device as defined in claim 29 in which said target molecule is a protein.

* * * * *